US012725310B2

(12) United States Patent
Wilander et al.

(10) Patent No.: US 12,725,310 B2
(45) Date of Patent: Sep. 1, 2026

(54) METHOD FOR IDENTIFICATION OF DIFFERENT CATEGORIES OF BIOPSY SAMPLE IMAGES

(71) Applicant: MM18 MEDICAL AB, Uppsala (SE)

(72) Inventors: Erik Wilander, Tällberg (SE); Sören Nygren, Åkersberga (SE); Tadas Marcinkevicius, Stockholm (SE)

(73) Assignee: CELLDA AB, Uppsala (SE)

( * ) Notice: Subject to any disclaimer, the term of this patent is extended or adjusted under 35 U.S.C. 154(b) by 475 days.

(21) Appl. No.: 17/292,039

(22) PCT Filed: Nov. 8, 2019

(86) PCT No.: PCT/EP2019/080706
§ 371 (c)(1),
(2) Date: May 7, 2021

(87) PCT Pub. No.: WO2020/094849
PCT Pub. Date: May 14, 2020

(65) Prior Publication Data

US 2021/0398321 A1 Dec. 23, 2021

(30) Foreign Application Priority Data

Nov. 9, 2018 (SE) .................................... 1851390-3

(51) Int. Cl.
*G06T 7/90* (2017.01)
*G06T 7/00* (2017.01)
(Continued)

(52) U.S. Cl.
CPC .............. *G06T 7/90* (2017.01); *G06T 7/0012* (2013.01); *G16H 30/40* (2018.01); *G16H 50/20* (2018.01);
(Continued)

(58) Field of Classification Search
CPC . G06T 2207/10024; G06T 2207/10056; G06T 2207/20081; G06T 2207/30024;
(Continued)

(56) References Cited

U.S. PATENT DOCUMENTS

2005/0037406 A1* 2/2005 De La Torre-Bueno .................... G06T 5/50 435/6.12
2005/0136549 A1 6/2005 Gholap et al.
(Continued)

FOREIGN PATENT DOCUMENTS

JP 2005535892 11/2005
JP 2014529158 10/2014
(Continued)

OTHER PUBLICATIONS

International Search Report and Written Opinion mailed Jan. 29, 2020; International Patent Application No. PCT/EP2019/080706 filed on Nov. 8, 2019. ISA/EP.

(Continued)

*Primary Examiner* — Kenny A Cese
(74) *Attorney, Agent, or Firm* — McDonald Hopkins LLC

(57) ABSTRACT

The present invention relates to a method for defining a colour range specific for a chosen category of samples, for use when identifying presence of cells of different categories in a tissue or cell sample. Further, methods for using the obtained colour range in selection of sample images comprising cells of a first category is also disclosed.

11 Claims, 30 Drawing Sheets

(51) Int. Cl.
*G06V 20/69* (2022.01)
*G16H 30/40* (2018.01)
*G16H 50/20* (2018.01)

(52) U.S. Cl.
CPC ............... *G06T 2207/10024* (2013.01); *G06T 2207/10056* (2013.01); *G06T 2207/20081* (2013.01); *G06T 2207/30024* (2013.01); *G06T 2207/30028* (2013.01); *G06T 2207/30081* (2013.01); *G06T 2207/30096* (2013.01); *G06V 20/698* (2022.01)

(58) Field of Classification Search
CPC . G06T 2207/30028; G06T 2207/30081; G06T 2207/30096; G06T 7/0012; G06T 7/90; G06V 20/698; G16H 30/40; G16H 50/20; G16H 50/70
USPC .......................................................... 382/162
See application file for complete search history.

(56) References Cited

U.S. PATENT DOCUMENTS

2005/0165290 A1* 7/2005 Kotsianti .............. G06T 7/0012 600/407
2005/0266395 A1* 12/2005 Gholap .................. G06V 10/46 702/19
2012/0115139 A1* 5/2012 Kuroda ................ C12Q 1/6886 435/6.14
2013/0108139 A1* 5/2013 Binnig ...................... G06T 7/11 382/133
2016/0123850 A1* 5/2016 Revie .................. G01N 21/278 435/40.52
2017/0178321 A1* 6/2017 Nieves Alicea ........ G06F 18/24
2018/0211380 A1* 7/2018 Tandon .................. G06V 20/69

FOREIGN PATENT DOCUMENTS

JP 2018502275 1/2018
WO 2010087112 7/2012
WO 2017087415 5/2017
WO 2018187629 A1 10/2018

OTHER PUBLICATIONS

Alex Skovsbo Jorgensen et al: “Using cell nuclei features to detect colon cancer tissue in hematoxylin and eosin stained slides,” Cytometry A, Wiley-Liss Hoboken, USA, vol. 91, No. 8, (Jul. 20, 2017), pp. 785-793, XP072333136, ISSN: 1552-4922, DOI 10.1002/CYTO.A.23175.
European Communication pursuant to Article 94(3) EPC, dated May 22, 2024, European Patent Application No. 19 801333.6 (7 pages).

* cited by examiner

METHOD FOR IDENTIFICATION OF DIFFERENT CATEGORIES OF BIOPSY SAMPLE IMAGES

CROSS-REFERENCE TO RELATED APPLICATION

This application is a 35 U.S.C. § 371 national stage application of PCT Application No. PCT/EP2019/080706 filed on Nov. 8, 2019, entitled "METHOD FOR IDENTIFICATION OF DIFFERENT CATEGORIES OF BIOPSY SAMPLE IMAGES," which claims priority to Swedish Patent Application No. 1851390-3 filed on Nov. 9, 2018, each of which are incorporated herein in their entirety by reference.

FIELD OF THE INVENTION

The present invention relates to a method for screening of biopsy sample images and identification of images relating to different categories of biopsy samples.

BACKGROUND OF THE INVENTION

Histological staining of biopsy samples is used in a variety of medical diagnosis procedures, such as identifying specific diseases or conditions related to changes at a cellular level.

Globally prostatic adenocarcinoma is the most common tumour type after breast carcinoma and consequently accurate histological diagnosis of prostatic adenocarcinoma is an important issue worldwide.

Prostatic adenocarcinoma is the most prevalent type of male cancer in Sweden, with over 10,000 new cases diagnosed every year. Similar statistics are seen throughout the developed countries. Prostatic adenocarcinoma constitutes around 30% of all male cancer cases and it occurs mainly in older men. Accordingly, 70% of the tumours are diagnosed in men 70 years of age and older. Over 2000 males die due to prostatic cancer every year and prostatic adenocarcinoma is the most common cause of death due to a malignant tumour among males in Sweden.

In Sweden an organised screening for prostatic adenocarcinoma has not been introduced, but middle aged and older men are regularly recommended screening for prostatic adenocarcinoma by performing blood sampling for analysis of PSA (Prostatic Specific Antigen). Elevated levels of PSA indicate an increased risk for prostatic adenocarcinoma. Males with elevated levels of PSA are recommended to attain a reception in urological surgery to obtain biopsies from the prostatic gland. These biopsies constitute the ultimate basis for the diagnosis of prostatic adenocarcinoma, even if other visual methods such as ultrasound and data tomography are also used.

In Sweden around 20,000 males are biopsied from the prostatic gland every year and since normally around 12 biopsies are collected in each male, approximately 250,000 histological glass slides from prostatic glands are examined each year. This is a time-consuming process as it is accomplished by light microscopy performed by doctors educated in surgical pathology. This conventional manual procedure and resulting diagnosis using microscopic examination of needle biopsies by medically trained professionals is referred to as the gold standard of diagnosis of prostatic adenocarcinoma. A majority of these biopsies (over 50%) display normal microscopic features, and may thus be identified as relating to a normal or benign tissue sample. If one or more of the samples taken from the same patient show indications of cancerous or malign cells, further assessment is needed. Therefore the batch of samples taken from each individual patient must also be assessed as a group.

Large intestinal (colon) cancer is a common type of cancer in both males and females. According to the Swedish cancer registry around 5 000 new cases per year are recorded. Colon cancer is mostly treated by radical surgery comprising the primary tumour in the intestinal wall and also the mesenterium containing the regional lymph nodes. In most operated specimens more than 15 lymph nodes can be identified in the fat tissue around the primary cancer of each case. This indicates that between 75 000-100 000 lymph nodes from individuals with colon cancer are examined microscopically each year in Sweden. Identification of lymph nodes metastases in colon cancer is of importance for staging of the tumour and for choice of post-operative treatment.

WO2013/064605 refers to the analysis of the expression of biomarkers in individual cells, and especially multiplex biometric images. US-B1-6297044 refers to an apparatus for testing lesions in the oral cavity, and to an anlaytical system comprising a programmed computer that can detect which cells require further examination due to e.g. a suspected cancerous condition.

At present a rapid progress in the use of digital techniques and automatic image analysis is observed in the field of medical analysis. It is likely that these techniques will play a much more dominating role as an adjunct in laboratory medicine in the near future. The inventors of the present invention has identified a need for an improved screening method, which provides for more effective screening, while maintaining accuracy.

SUMMARY OF THE INVENTION

An object of the present invention is to provide a method for rapid screening of tissue biopsies by computer analysis of digital images after application of immunohistochemical staining of the biopsies.

Another object is to provide a fast and efficient method for identification and sorting out of biopsies not needing further assessment and in that manner markedly reduce the number of biopsies demanding a visual (microscopic) inspection by a pathologist. As mentioned above, this would reduce the workload requiring medically trained personnel by more than 50%. In addition, the response time to the patient would thereby also be reduced.

A further object is to provide such a method which is cost effective while having an extremely high validity.

The above-mentioned objects are achieved by the present invention according to the independent claims. Preferred embodiments are set forth in the dependent claims.

In a first aspect, a method for defining a colour range for use when identifying presence of cells of different categories in a tissue or cell sample is disclosed, the method comprising the steps of:

a) dividing a plurality of samples into at least one batch, and for each batch staining and classifying each sample into a first and a second category;
b) obtaining a sample image of each sample;
c) defining a colour range for each batch of sample images identifying samples belonging to the first category;
d) evaluating the sample images in each test batch and adjusting the colour range for each test batch to ensure all samples belonging to the first category are correctly categorized; and e) selecting at least one operational threshold and storing the adjusted colour range for use when identifying cells belonging to the first category in a tissue or cell sample.

Typically, in step a), the samples are preclassified and/or the classification of samples is performed by medically trained personnel, who will assess each sample and categorise it as one of the two categories, based on different colourings of the categories, and wherein the first and second category represent non-normal and normal cell samples, respectively, such as malign and benign samples, or different stages of a disease, such as cancer.

Typically, in step d), adjustment of the colour range is made by by excluding colour values seen in the second category of samples.

In a second aspect, a method is disclosed for selection of tissue or cell samples comprising cells of a first category, wherein the method comprises retrieving or predetermining (S21) at least one threshold and a colour range as described above, wherein the method further comprises:

A) staining at least one patient sample comprising tissue and/or cells;

B) obtaining a sample image of each patient sample;

C) determining a total pixel number, such as a sum of abnormal pixel weights or a ratio of pixels, in the colour range for each patient sample image;

D) classifying each patient sample as belonging to the second category if the total pixel number in the sample image is below the retrieved or predetermined at least one threshold, or classifying each patient sample as belonging to the first category if the total pixel number in the sample image is above or equal to the retrieved or predetermiend at least one threshold; and E) removing patient samples belonging to the second category from review.

As will be further explained in this disclosure, the total pixel number can be derived in different ways, in line with the embodiments of this invention.

In one embodiment, the summed abnormal colour pixels is typically weighted for distance to red colour (indicating blood), and then the result is divided by the total number of sample pixels, so that a ratio of pixels is obtained.

In another embodiment the total number of sample pixels is not used, but instead the nearby abnormal colour pixels (also weighted for distance to blood, but without dividing by total number of sample pixels) is summed. In this embodiment, the steps (after colour filtering) will typically be:

1. cancer colour pixels are grouped by distance into groups (thus there can be several separate groups in the same image),
2. the cancer pixel weights for each group are summed separately and
3. each group result is compared (separately) to the predetermined threshold. If even one group result is >=threshold, then the whole sample is classified as first category (non-normal). If all groups results are <threshold, only then classified as second category (normal).

In this embodiment, it is especially important to determine how the pixels are grouped (over how large distances) and the level(s) of the threshold value(s).

SHORT DESCRIPTION OF THE APPENDED DRAWINGS

FIG. 1*a* and 1*b* show exemplary images of histologically stained tissue samples, used in a method for defining a colour range for use when identifying presence of one of at least two categories of cells in a tissue or cell sample.

Figure 1A:
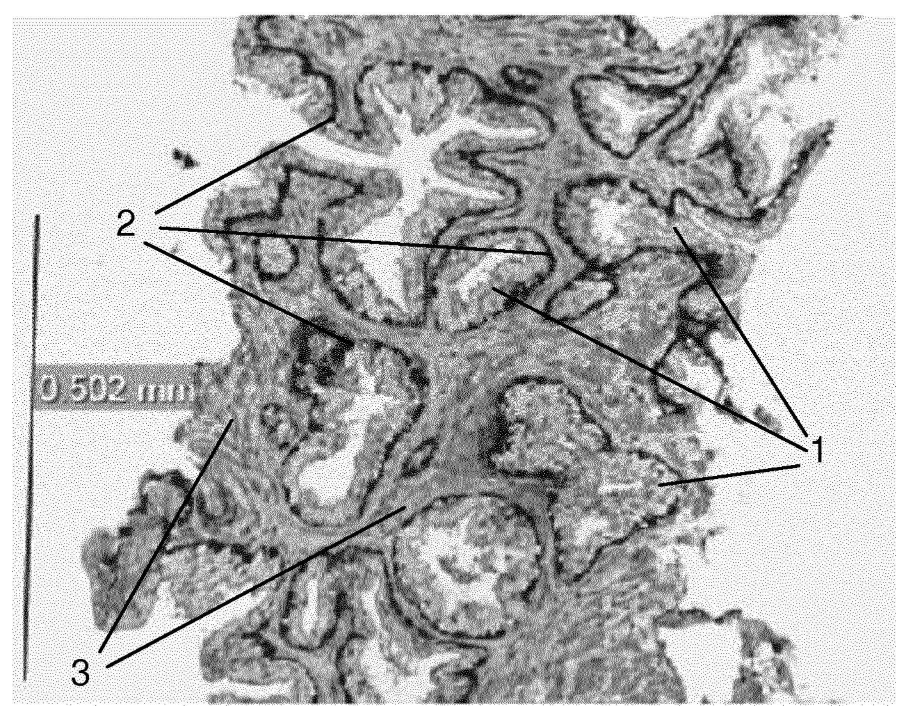

FIG. 17-27 refers to Example 4 (Cancer grouping into blobs for absolute valuation program flow).

FIG. 28-37 refers to Example 5 (Sample edge cutoff program flow).

DEFINITIONS

The term "total pixel number" refers to the value that is compared to a predetermined or retrieved threshold value in order to determine whether a sample image or part of a sample image refers to normal or non-normal sample. The "total pixel number" can be e.g. "a sum of abnormal pixel weights" or "a ratio of pixels".

The "sum of abnormal pixel weights" is used for cases where a sum of pixel weights in a group of pixels is compared to a first threshold value, and where a sum of pixel weights in all groups is compared to a second threshold value, where the second threshold value typically is higher than the first threshold value. Thus, when using the "sum of abnormal pixel values" one typically identifies abnormal pixels (cancer pixels vs the rest) and then discard their colour values and instead assign them weights (distance to blood) as their new values. At the time where the pixel weights are summed, there is no original pixel value information left, only the weight values for each pixel, in short their "weights". Thus, the term "sum of abnormal pixel weights".

The "ratio of pixels" is used for cases where a pixel value (optionally weighted for the distance to blood), comprising the number of pixels falling within the selected criterias, is divided with the total number of pixels in the sample image.

By "pixels falling within the selected criterias" is meant pixels remaining after background and colour filtering, such as cancer pixels. Such pixels can also be defined as "abnormal pixels".

DETAILED DESCRIPTION

One of the aims of the invention is to effectively eliminate a large proportion of samples from a pool of samples to be analysed, and thus free up resources and save time. This will reduce the amount of manual workload requiring medically trained personnel by at least 50%.

One effect of greatly reducing the manual workload requiring medically trained personnel, is a quicker response time to the patient, which in turn leads to an earlier identification of cancer or other diagnoses in patients, allowing for quicker initiation of treatment. Naturally, it also results in faster identification of e.g. non-cancer or normal samples, and thus improves the quality of life for those involved.

Another positive effect is an improved work environment and less stress for the medically trained personnel within the histopathology and pathology fields. Having the personnel focus on the positive or complex samples, by eliminating a large portion of the samples not needing further evaluation, will improve use of resources in health care.

In the following, an exemplary application of a method wherein a colour range is defined that correlates to a specific category of samples is disclosed. The defined colour range is thereafter used on a another batch of samples in a further method to classify samples into at least two categories.

The methods disclosed herein are described in terms of identifying and selecting and/or separating non-normal cell samples from normal cell samples in a large batch of histologically stained cell samples taken by biopsy of the prostate gland in male patients. However, as will be shown herein, the disclosed methods may be applied to essentially any type of stained cell samples wherein one category of cell samples differs in colouring from another category of cell samples. It follows that any type of staining of cell or tissue samples may be used in the disclosed methods, as long as the staining results in different colourings of the categories to be identified and distinguished from each other.

Examples of other applications are various other types of cancer, other diseases or any procedure where a batch of images need to be sorted into different categories based on the presence of a quantifiable colour range in one category and not in the other category.

More specifically, the methods disclosed herein may be applied broadly within the field of digital pathology. Thus, other tissues from which a sample can be stained and colour differences in the stained sample can be analysed in accordance with the claims of this invention, are within the scope of this invention.

Known methods of evaluating stained tissue samples, for instance staining techniques that are specific for either normal or non-normal cells, or cells of different developmental stages, may be used in many different situations. One example, illustrated herein, is for determining if a sample includes cells that have transformed from normal cells to cancer cells. Known techniques typically rely on identifying both structural differences in cell samples as well as differences in the colour distribution of the stain. When being assessed manually, this is very time consuming process. The present disclosure provides a method of identifying unique characteristics, using only differences in colour parameters in stained and scanned images of one category of samples compared to another category of samples, and thereafter using these differences to reliably separate the different categories of samples from each other.

Due to inherent variations of staining results, the varying nature of cancer cell structure and appearance, and well as the composition of the tissue in the sample, there will naturally be samples that are difficult to classify, even for a medically trained person. However, if the larger part of samples, e.g. those that are quickly identified as only comprising normal cells, or any chosen category not needing further assessment, could be eliminated from further assessment, the workload will be significantly reduced, leading to a faster overall assessment of samples.

The present inventors have realised that an effective manner of achieving a substantially less amount of samples that require manual assessment, is to use a method wherein a colour range is defined that correlates to a chosen category of samples. This colour range is defined based on the colour of individual pixels in scanned images of a pre-classified batch of tissue samples. Threshold values may be defined to guarantee that no samples of the specific category are eliminated from further evaluation.

Once the defined colour range is specified, it may be used to classify samples in another batch of samples, e.g. a new batch of samples to be assessed, wherein the samples are to be classified as belonging to a first or second category. The samples of the category needing further assessment are preferably thereafter reviewed in a final step by medically trained personnel, to determine whether each sample, or rather the collective batch of samples from a single patient, are indicative of a disease or condition.

Figure 1B:
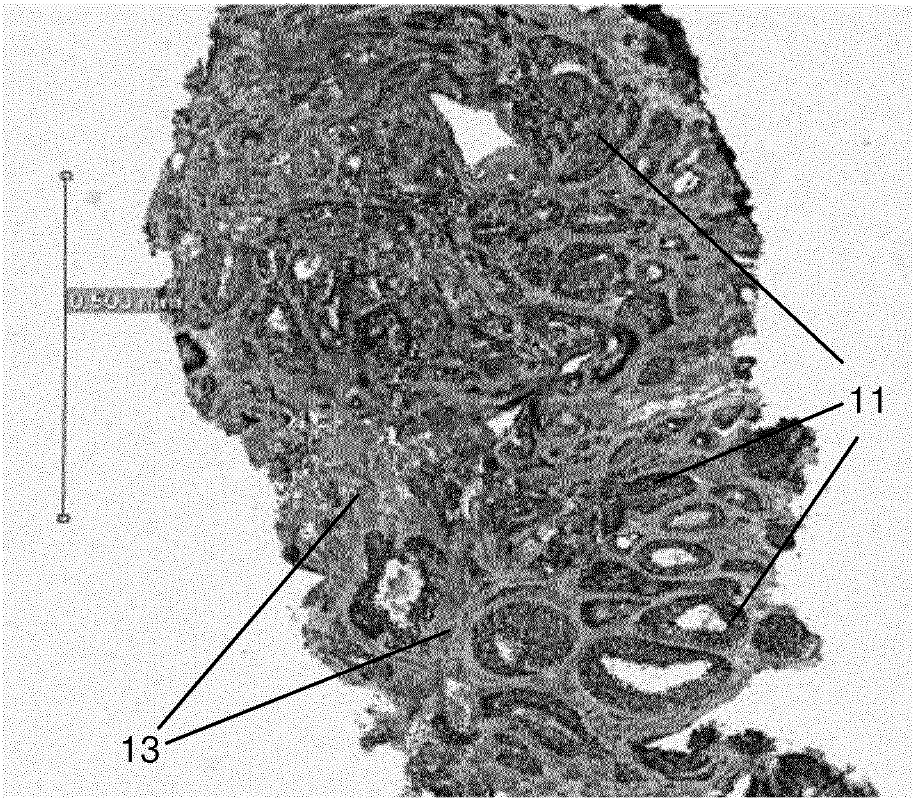

FIGS. 1*a* and 1*b* show exemplary images, representing two different categories, used in a method for defining a colour range for use when identifying presence of one of the categories of cells in a tissue or cell sample. The images may also be representative of images used in a method for categorising samples using such a defined colour range and thereafter selecting one category.

The prostate biopsy samples in FIGS. 1*a* and 1*b* have been fixed, sectioned and stained as described in Example 1 below. The staining pattern using these particular antibodies (antibodies to P504S, p63 and CK5) results in two colours, brown and red, being fundamentally different in normal prostatic gland (FIG. 1*a*) and in prostatic adenocarcinoma (FIG. 1*b*).

FIG. 1*a* shows a sample of normal prostatic gland after the above described staining (here shown in grayscale). The glandular epithelium 1 is unstained and the peripheral myo-epithelial cells 2 are stained red (here seen as a darker colour). The tissue has a blue background staining 3 representing the connective tissue around the glands.

FIG. 1*b* shows a stained sample of prostatic adenocarcinoma (here shown in grayscale). The glandular epithelium is transformed to adenocarcinoma cells 11 and shows a brown staining (here seen as a semi-dark colour). The peripheral myo-epithelial cells have disappeared, as well as the red staining occurring in normal prostatic gland. The tissue has a blue background staining 13 representing the connective tissue around the glands.

Thus, this particular type of staining of prostate gland cells shows a clear colour difference, in this case also visible to the naked eye in a microscope. Normal prostate glands show a substantial amount of distinctive red staining while adenocarcinoma samples lack the red colour, but show a substantial amount of distinctive brown staining. Notably the two examples shown in FIGS. 1*a* and 1*b* are typical of completely normal tissue and completely transformed tissue. In other samples, some part of the sample may be transformed and some parts may be normal. Further, often other types of cells and material may be present in small amounts, such as droplets of blood or other bodily fluid, or other types of cells that were picked up when performing the biopsy. However, it is clear that the presence of cancer cells results in a brown staining in a sample, and that this brown staining is not seen in samples without cancer cells.

In the following an exemplary application of a method will be described. See Example 1 and Example 2 below for further rounds of application of the methods, with larger sample batches, and for application of the methods using other types of cells and staining techniques.

In a first study, sample images of a batch of approximately 130 samples pre-classified into cancer (malign) or normal (benign) samples were obtained in HSV image format. As is known in the art, the colour of each pixel in such an image is defined by three values: “Hue” (possible range from 0 to 179), “Saturation” (possible range 0 to 255) and “Value” (possible range 0 to 255). Thus, the colour of individual pixels in each sample image are assessed.

A first manner of defining a colour range specific for presence of prostate cancer cells is to define it as all HSV values in the “brown” range, based on the knowledge from the chosen staining type, as described above, of brown colour being specific for presence of cancer or malign cells. For example, as a starting point in defining a colour range specific for non-normal cells, a colour range of brown colour, defined by HSV values of Hue [8 to 28], Saturation [30 to 255] and Value [31 to 200], may be chosen. In another embodiment, ranges for cancer colour may be Hue [175 to 179], Saturation [60 to 130] and Value [40 to 120] and/or Hue [0 to 22], Saturation [60 to 190] and Value [40 to 130]. For example, both these ranges may be used, so that any colour falling within any one of these ranges is considered cancer colour.

The colour range specific for presence of non-normal cells may be further defined by removing the individual values within the above initial range, in this case being brown colour, that are nonetheless present in normal images, due to e.g. the overlap of other colours in the image. This may be done by first identifying all pixels in normal images that fall within the above initial brown range. These pixels are counted in all scanned normal images, and each colour value that appears in these pixels more than a predefined number of times (Nx) is removed from the non-normal colour range above, and thus considered to be defined as a colour defining normal images. Nx may vary based on the number of images processed and number of pixels in each image.

The obtained colour range specific for presence of non-normal cells is stored for further use in a method for selection of tissue or cell samples comprising non-normal cells, using the determined colour range.

As a further application, the methods disclosed herein may be applied to identifying stages of colon cancer in samples taken from regional lymph nodes in the mesenterium. This is described in detail in Example 2 below. Identification of lymph nodes metastases in colon cancer is of importance both for staging of the tumour and for choice of post-operative treatment.

The above described method may thus be applicable to many different types of stained cell or tissue samples.

Figure 11:
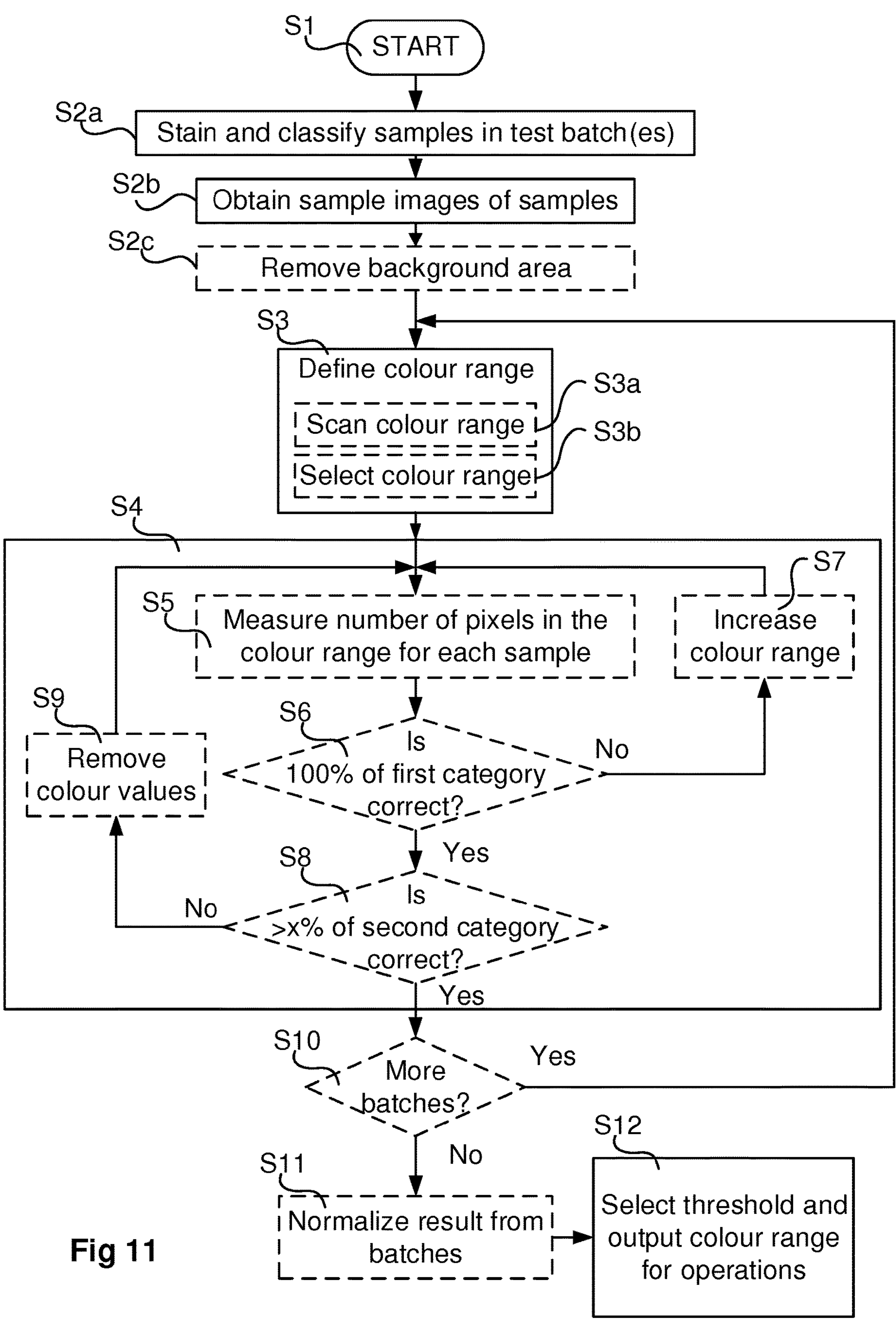
FIG. 11 illustrates a flowchart of a method for defining a colour range for use when identifying presence of cells of a specific category in a tissue or cell sample.

Thus, in a first aspect, as seen in FIG. 11 a method is disclosed for defining a colour range for use when identifying presence of cells of a specified category in a tissue or cell sample. The method comprises:

a) dividing a plurality of samples into at least one batch, and for each batch staining and classifying each sample into a first and a second category (step S2*a*);
b) obtaining a sample image of each sample (step S2*b*);
c) defining a colour range (step S3) for each batch of sample images identifying samples belonging to the first category;
d) evaluating the sample images in each test batch and adjusting the colour range for each test batch to ensure all samples belonging to the first category are categorized correctly (step S4); and
e) selecting at least one operational threshold and storing the adjusted colour range (step S12) for use when identifying non-normal cells (or cells belonging to the first category) in a tissue or cell sample.

As described above, this method is used to define a colour range at a pixel level in images of samples containing a first category of samples, while excluding colour values seen in a second category of samples. This is done on at least one batch of samples which has been pre-assessed and categorized by medically trained personnel. The staining of samples may be performed by known methods or new staining techniques. The final classifying step in step S2*a* is typically thereafter performed by medically trained personnel, who will assess each sample and categorise it as one of two categories. However, it is also conceivable that samples are taken from known sources of two different categories of tissue or cells, i.e. pre-classified, and thereafter stained.

As in the examples above, the categories may e.g. be a first category being malign samples and a second category being benign samples. A malign sample is one where at least one malign or cancerous cell is identified. A benign sample has no cancerous cells.

It must be noted herein that the terms defining absolute categories such as malign or benign samples are only used in a final step of a testing, assessment and diagnosing procedure of a sample, when it is absolutely certain, i.e. according to the golden standard, that the samples are correctly assessed.

The categories may also be different stages of a disease, such as cancer, or other differences in samples types that cause different colour distribution in prepared cell or tissue samples.

The above disclosed method of defining a colour range and an operational threshold is intended for later use in another method of assessment of other sample batches. The method of assessment or selection will be described in detail further below.

However, in early stages of an assessment procedure of non-classified prostate gland or other samples, when there is a risk of some samples incorrectly being categorized, it is preferred to name the categories normal and non-normal. In the presented methods herein, it is envisioned that initially a non-normal category may include malign samples, as well as samples with incorrect staining results, due to either too much colour or too little colour overall, and also samples including other types of abnormal cell structures.

After step S2*a* in FIG. 11, each image is scanned to obtain a corresponding sample image (Step S2*b*) in e.g. HSV format. These images are used for the further steps of defining and preferably adjusting the defined colour range.

As a preferred but optional step, the pixels corresponding to background colour, i.e. non-tissue area, may be removed from further calculations (step 52*c*), such that only tissue area is part of the assessed sample area. This may be done by excluding all pixels in an image that are above a certain brightness level, e.g. above brightness value 200, or 210, or 220 or any other suitable brightness value. An example of removing all pixels above the brightness vale 210 may be seen when comparing FIG. 2 and FIG. 3. As a further optional step, pixels of uncertain colour due to extremely intense colouration may be excluded from the sample image, in order to not include uncertainties in the following calculations. This may be done by excluding all pixels in an image that are below a certain brightness and saturation value, such as below 30, 31, 32, 33 or any other suitable brightness value.

A colour range may be defined (step S3) by selecting a colour range based on empirically found colour distribution of stains in particular cell types, and thereafter further refined in step S4 to ensure all samples belonging to the specified category are found. As an example in the case of prostate biopsies above, the brown colour range was chosen as a starting point, and further refined to ensure that no samples of the first category are missed.

As an alternative, the definition of the colour range may be performed by scanning part of, or the complete colour spectrum, of an image to identify and select a suitable colour range, such colour being distinctive or indicative for the first category of samples when compared to the second category. It is further conceivable that such differences may be only identifiable by a digital scanner system, and not visibly perceptible. In any case, a colour range is selected such that all samples belonging to the first category are identified.

According to some embodiments step S3 may further comprise defining a second colour range, e.g. in the red colour range, used to identify anomalies to prevent samples of the second category to be categorized as belonging to the first category. This process is described in more detail in connection with FIG. 13.

After defining the colour range, the colour range is evaluated and adjusted (step S4) to ensure all samples belonging to the first category are categorized correctly. This step may be performed by first measuring the number of pixels in the selected colour range in each sample image (step S5). This is preferably done with background pixels removed, as described above, such that only tissue area of an image is included. All pre-classified images belonging to the first category may be assessed that they fall within the colour range (step S6). If this is not the case, the colour range is increased, i.e. further values added, until all samples of the first category fall within the adjusted colour range (step S7).

Thereafter, optionally all pre-classified images belonging to the second category are assessed if they fall outside the adjusted colour range (step S8). In this step it is not necessary to achieve a complete compliance, as it is expected that some samples of the second category might fall within the colour range, and if this is the case, they may be removed at a later stage. Hence, a threshold value may be selected in step S8, such that it is assessed if more than a certain percentage of the sample images of the second category fall outside the selected colour range. This threshold may be any percentage, preferably higher than 90%, more preferably 95% or higher.

If the result of step S8 is that there are still less than the chosen threshold percentage of samples of the second category that fall outside the colour range, the colour range may be adjusted, e.g. by removing specific colour values, and steps S5 to S8 repeated.

The finally obtained colour range specific for a chosen category of samples is thereafter stored (step S12) for use to assess other batches of non-categorised samples, or to verify samples in pre-classified batches. Furthermore an operational threshold value is selected based on the stored colour range and the measured number of pixels in the colour range for each sample.

Figure 10:
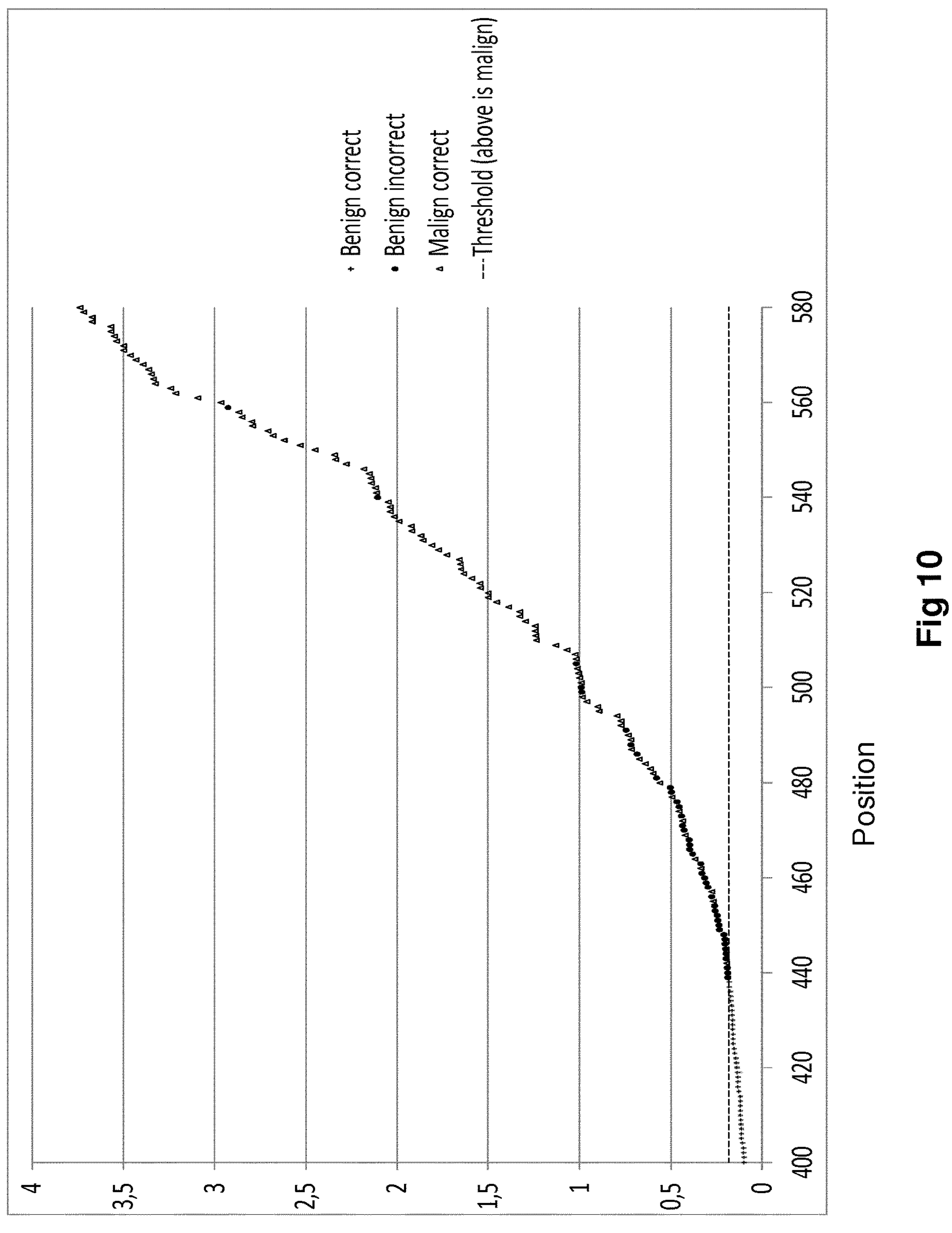
FIG. 10 shows a graph of a batch of histologically stained samples as a function of malign indication value within a pre-defined colour range.

An example of a curve used for determining the operational threshold value is depicted in FIG. 10, which illustrates a graph of a batch of histologically stained samples as a function of a first category (e.g. malign) indication value within the selected colour range.

All stained samples are processed to determine a malign indication value and assigned a position as a function of the malign indication value. The process to determine the malign indication value is in its simplest form a measurement of the number of pixels within the selected colour range for each sample. In a more advanced process, anomalies are taken into considerations when determining the malign indication value for each sample, e.g. by using the process described in connection with FIG. 13.

An example of determining a malign indication value is as follows.

Assume an image having 100 pixels within the selected saturation and brightness range (malign+benign+blood). The image having 4 malign pixels (within cancer colour range) and 95 benign pixels (outside cancer colour range) and 1 red pixel (indicating blood, and is considered to be benign). If all samples have 100 pixels within the selected saturation and brightness range, the number of malign pixels may be used as a malign indication value.

However, this is seldom the case and below are three different examples A, B and C of weighted pixel calculation or weighted anomaly pixel calculation described.

EXAMPLE A

Weighted pixel calculation will yield an malign indication value for the sample to be 4/100=0.04. The maximum malign indication value is 1.0 if all pixels are malign.

EXAMPLE B

Weighted anomaly calculation is obtained by assigning each pixel a weight from 0-255. This weight is inversely proportional to the distance between its owner pixel and the red-pixel (many false cancer-colour pixels happen closest to blood). A mathematical formula is used to determine the weight of each pixel:

$$w_d=(d*a_1)-a_2,$$

where $a_1$ and $a_2$ are constants and d is the distance between the malign pixel and the red pixel. In this example $a_1=3.8$ and $a_2=10$. However, other constants may be used depending on use-case, The first malign pixel has a distance of 10 pixels to the red pixel, and the weight for the first pixel is $w_1=(10*3.8)-10=28$. The second pixel has a distance of 20 pixels to the red pixel, and the weight for the second pixel is $w_2=(20*3.8)-10=66$. The third pixel has a distance of 50 pixels to the red pixel, and the weight for the third pixel is $w_3=(50*3.8)-10=180$. The fourth pixel has a distance of 100 pixels to the red pixel, and the weight for the second pixel is $w_4=(100*3.8)-10=370$, which is limited to the maximum value 255. Note: image 5 shows where the red pixels are (in a much larger real image) and image 8 shows all pixel weights as brightness value (black=0 weight, white=255 weight).

The malign indication value is the sum of the weights divided by total number of pixels=$(w_1+w_2+w_3+w_4)/100=(28+66+180+255)/100=5.29$, as illustrated in FIG. 10. This value may also be divided by the maximum weight 255, which will yield a malign indication value of 5.29/255=0.020745 which may be compared to the result from Example A.

The values on the Y-axis may be normalized in order for the maximum malign indication value to correspond to 100% (not shown in FIG. 10).

When the malign indication value has been calculated for all the samples, these are presented in a graph (as FIG. 10) and an operational threshold value 100 is selected to ensure that all malign samples are categorized correctly. Only samples of the second category (e.g. benign) will be below the operational threshold value 100. In this example the operational threshold value is set to 0.180392 to ensure "Gold standard".

EXAMPLE C

The method of Example B may be performed with updated/other numbers:

Weighted anomaly calculation is obtained by assigning each pixel a weight from 0-255. This weight is inversely proportional to the distance between its owner pixel and the red-pixel (many false cancer-colour pixels happen closest to blood), A mathematical formula is used to determine the weight of each pixel:

$$w_d=(d*a)-a_2,$$

where $a_1$ and $a_2$ are constants and d is the distance between the malign pixel and the red pixel. In this example $a_1=7.0$ and $a_2=10$. However, other constants may be used depending on use-case.

The first malign pixel has a distance of 10 pixels to the red pixel, and the weight for the first pixel is $w_1=(10*7.0)-10=60$. The second pixel has a distance of 20 pixels to the red pixel, and the weight for the second pixel is $w_2=(20*7.0)-10=130$. The third pixel has a distance of 50 pixels to the red pixel, and the weight for the third pixel is $w_3=(30*7.0)-10=200$. The fourth pixel has a distance of 100 pixels to the red pixel, and the weight for the second pixel is $w_4=(100*7.0)-10=690$, which is limited to the maximum value 255.

The malign indication value is the sum of the weights divided by total number of pixels$=(w_1+w_2+w_3+w_4)/100=(60+130+200+255)/100=6.45$. This value may also be divided by the maximum weight 255, which will yield a malign indication value of 6.45/255=0.025294 which may be compared to the result from Example A.

The values on the Y-axis may be normalized in order for the maximum malign indication value to correspond to 100%.

When the malign indication value has been calculated for all the samples, these are presented in a graph and an operational threshold value 100 is selected to ensure that all malign samples are categorized correctly. Only samples of the second category (e.g. benign) will be below the operational threshold value 100. The operational threshold value is set to ensure "Gold standard".

After evaluation and adjustment of the colour range (step S4), an optional step is to assess further batches (step S10) of sample images of similarly stained pre-classified samples, after which steps S3 and S4 are repeated for each batch before storing the final obtained colour range. In other words, defining, evaluating and adjusting the colour range may be performed based on each further batch, and the results of all batches combined before storing the final resulting colour range and threshold (step S12).

As is known in the field of histology, stained samples may vary in saturation and distribution of colour. Therefore, a reference field may be included, either at least once per stained batch (staining event), or on each glass slide where two or more samples are fixed. This reference field will allow for harmonisation of different batches in comparison to each other. Thus, an optional step of the method for defining a colour range is to include a similarly stained reference field adjacent to each sample or at least on the same sample slide, and using this to normalize (step S11) the adjusted colour range for each batch based on the colour of the reference field before storing the final resulting colour range. One example of a staining of a sample for a reference field is shown in Example 3.

After defining and saving a colour range specific for a chosen category of samples, as described above, this colour range may be used to assess another batch of samples, in order to identify and select the samples belonging to the chosen category. As an example, this process will be described for selecting non-normal cell samples in a batch of biopsy samples of prostate gland, and thus being able to remove all samples only showing normal colour characteristics from the batch. This process can be based either on the sums of adjacent pixel weights, for pixels falling within the selected criterias, being compared to selected threshold(s), or relative pixel counts, i.e. ratio of pixels, optionally weighted, falling within the selected criterias, to the total number of sample pixels, being compared to the selected threshold(s). In the context of this disclosure both alternatives are referred to as total pixel number.

Figure 2:
FIG. 2 illustrates an exemplary image of a histologically stained tissue sample used in a method for selection of tissue or cell samples comprising non-normal prostate gland cells.
Figure 3:
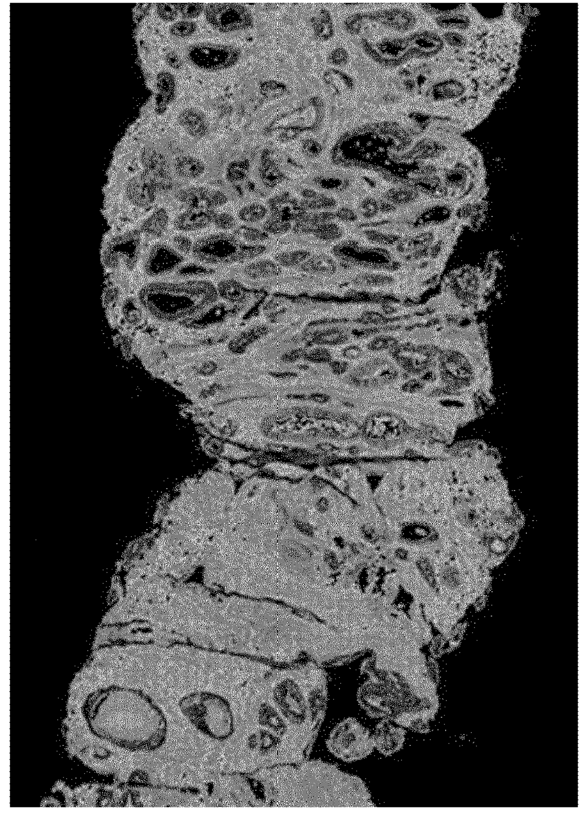
FIGS. 3 to 9 illustrate images of the sample of FIG. 2 after application of the various steps of a method for selection of tissue or cell samples comprising non-normal prostate gland cells.

FIG. 2, as mentioned above, show an exemplary image of a stained prostate biopsy sample. To isolate pixels relating to tissue sample, as described above, background pixels are removed by removing pixels above a certain brightness value, e.g. 205. Further, pixels that are difficult to measure colour values of colour are removed by removing pixels with brightness value below 31, because at low brightness values, noise in the image constitutes a much larger portion of the pixel value and makes hue subject to significant variations from noise. Also there would be significant rounding errors in hue calculation. Removing boundary pixels is illustrated in step S30 in FIG. 13. FIG. 3 shows the same sample as in FIG. 2 after bright and dark pixels are removed.

The total number of pixels in the patient sample, Sample Area (SA), i.e. remaining after bright and dark pixels have been removed, is counted, in step S31. At this stage, it is possible to use the previously defined and retrieved colour range, and remove the pixels outside the colour range (step S32), and count the number of pixels within the colour range in the patient sample, Cancer Area (CA), step S33.

The ratio of sample pixels falling within the defined colour range is calculated by dividing the number of pixels falling within the defined colour range, CA (illustrated in FIG. 4, wherein the pixel within the colour range are illustrated as white pixels) by the total number of pixels of patient sample, SA (FIG. 3) for each sample image, step S34. This ratio, also called malign indication value, is an indication of the classification of the sample. If the ratio of pixels CA/SA within the pre-defined colour range in the image is above the operational threshold value selected in step S12, the sample is classified as a non-normal sample. On the other hand, if the ratio is below the operational threshold value, it is classified as normal.

The above ratio calculation and classification may be repeated for each sample image in a batch. Thereafter non-normal sample are selected for further review by medically trained personnel.

As it is common, especially in certain forms of cancer, such as prostate cancer, that not all samples from an individual patient show cancer cells, samples from each patient are preferably aggregated. In the group of samples from the same patient, if at least one of the samples is classified as non-normal, the entire group of samples from that patient is classified as non-normal, and will be reviewed by medically trained personnel for assessment of the presence of cancer.

Figure 5:
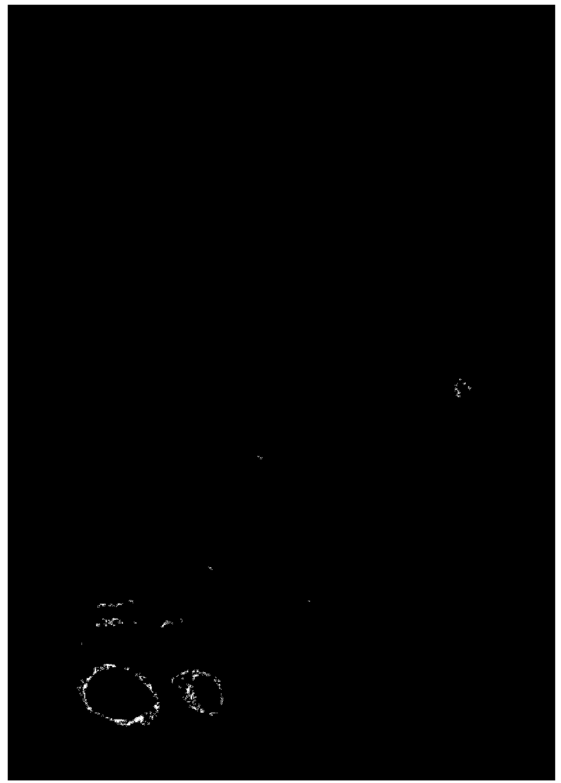

A common occurrence in prostate biopsies is the presence of a small amount of blood in the sample, as mentioned above. As the colour of such blood in a stained sample is red with a brown periphery, any brown found near red colours is less likely to indicate cancer. Thus, the calculated ratio of sample pixels falling within the defined colour range may be adjusted by decreasing the influence of any brown pixels near the red pixels. As an example, any red pixels in the sample image of FIG. 3 are identified, by finding pixels within the red colour spectrum of Hue [173 to 179], Saturation [168 to 255] and Value [35 to 180]. These pixels have been extracted from the sample image and converted to white colour in FIG. 5. This process is illustrated as an optional step S35 in FIG. 13. In other embodiments, ranges for red colour may be Hue [171 to 176], Saturation [175 to 255] and Value [90 to 101] and/or Hue [171 to 179], Saturation [168 to 255] and Value [102 to 180]. For example, both these ranges may be used, so that any colour falling within any one of these ranges is considered red colour.

The influence of all brown pixels is decreased as a function of the distance to a red pixel, as described in connection with FIG. 10 above. The influence of each red pixel (shown in FIG. 5) on the pixels shown in FIG. 4 may be calculated as explained above, but this is very time consuming. The process described in connection with FIGS. 6-9 illustrates an optional process to calculate the weight of each pixel in FIG. 4 as a distance to red pixels shown in FIG. 5.

Figures 6, 7:

FIG. 6 illustrates the result of a process called "dilation", which increases the pixels within the red colour range. The dilated image (as illustrated in FIG. 6) is used as input to generate a distance-transform image where pixel values represent distances from the white dots. For example, a pixel adjacent to white will have value "1" (distance=1 pixel); a pixel that has one other pixel between it and the white pixel will have value "2" (distance 2 pixels), and so on. Note that the calculation uses shortest (hypotenuse) distance, e.g. 10 pixels down and 23 pixels to the right would give value "25" (and not "33"). The distance-transform image is illustrated in FIG. 7, which is made from the dilated image in FIG. 6. This method to achieve this is called "Euclidean distance transform".

Figure 4:
Figure 8:
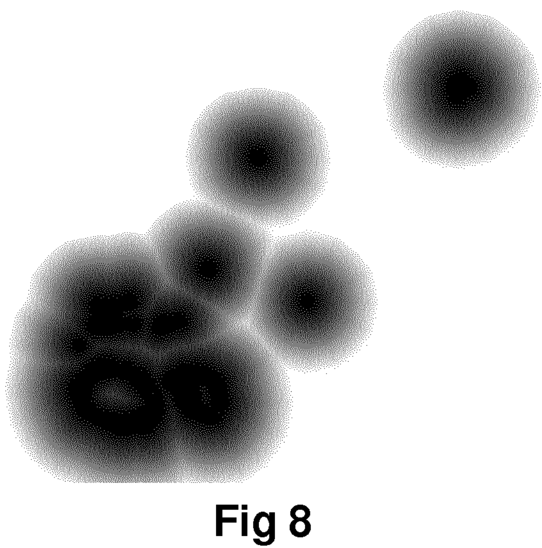

The distance transform image may be used directly to decrease the influence of any brown pixels near the red pixels by multiplying the distance-transform image with the image of FIG. 4 (illustrating pixels within the colour range). However, it has been found that a more reliable and consistent result may be achieved if the distance transform image is scaled by multiplying each pixel value with a number "k" (wherein "k" is in the range 3.6-4.0, preferably 3.8), wherein each pixel value is multiplied separately. All pixel values increase "k" times, i.e. a pixel value increases from 2 to k*2=7.6 if k=3.8. and the maximum value of 255 is reached more quickly. FIG. 8 illustrates the distance transform image after multiplied with k=3.8.

As explained above, the distance transform image (scaled or not) is multiplied with a binary 0/1 image (as in FIG. 4, where pixel value 1 is non-normal and pixel value 0 is normal) to obtain an image where pixels represents not only the location of potential malign cells but are also weighted by the distance from red colour. After multiplication, pixel values will range from "0" up to "255" (non-normal and far from red), as illustrated in FIG. 9 and this corresponds to the optional step S36 in FIG. 13.

Figure 9:

CA is the sum of all pixel values in the image of FIG. 9. Each pixel may contribute up to 255 when calculating CA, which means that the ratio CA/SA will be larger and the operational threshold have to be increased accordingly. These optional steps improves the process to correctly classify normal samples by more than a factor three.

Figure 12:
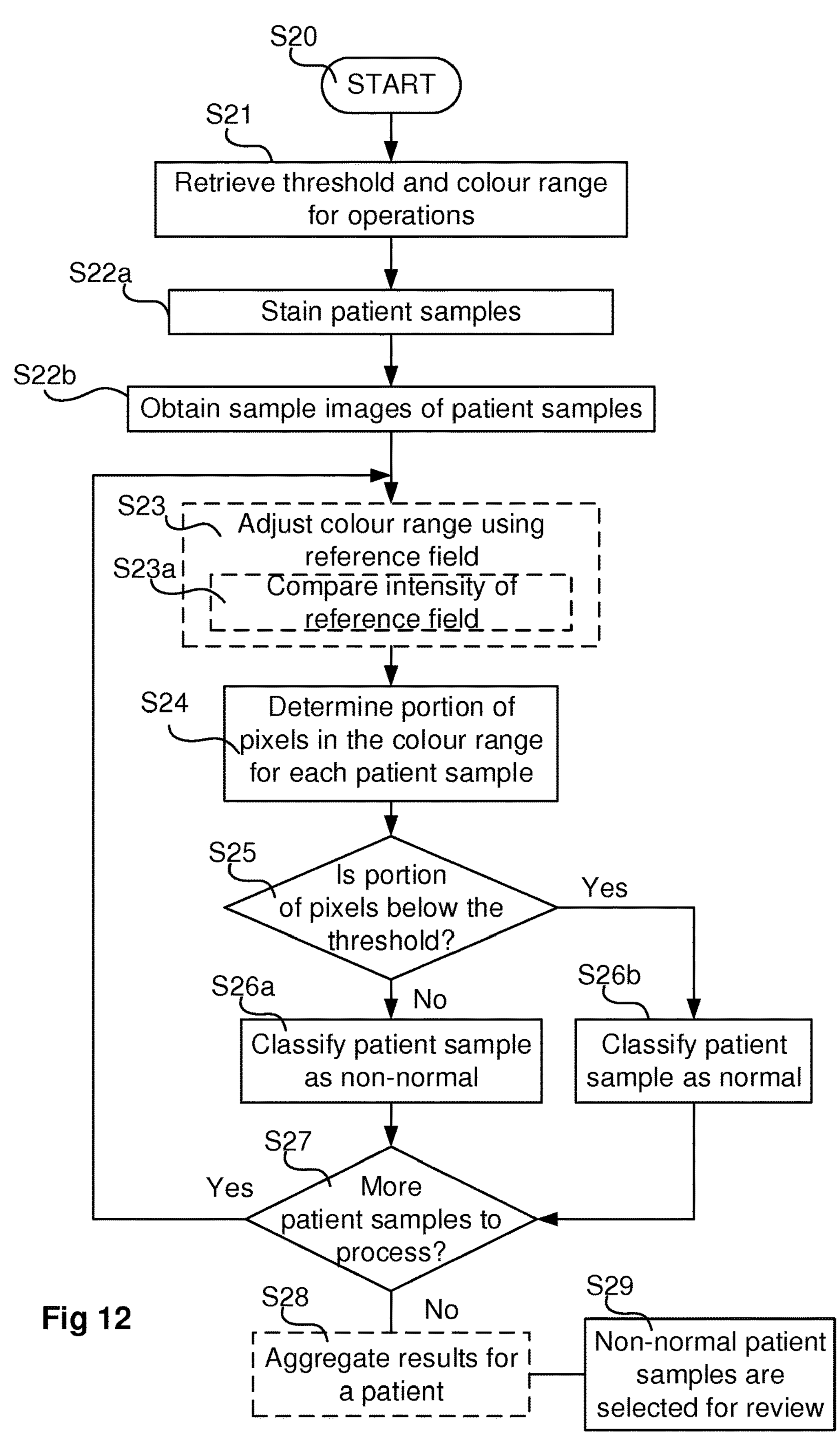
FIG. 12 illustrates a flowchart of a method for selection of tissue or cell samples comprising cells of a specific category.

Hence, in a further aspect, as illustrated in FIG. 12, a method is disclosed for selection of tissue or cell samples comprising non-normal cells, i.e. belonging to a first category. The method comprises retrieving, S21, or predetermining at least one threshold and a colour range determined as described above, and the method further comprises the steps of:

A) staining at least one patient sample comprising tissue and/or cells, step S22*a;*

B) obtaining a sample image of each patient sample, step S22*b;*

C) determining a total pixel number, such as a sum of abnormal pixel weights or ratio of pixels in the colour range for each patient sample image, step S24;

D) classifying each patient sample as belonging to the second category if the total pixel number in the sample image is below the at least one retrieved or predetermined operational threshold value, or classifying each patient sample as belonging to the first category if the sum of abnormal pixel weights or the ratio of pixels in the sample image is above or equal to the at least one retrieved or predetermined threshold value, steps S25, S26*a*, S26*b*; and E) removing patient samples belonging to the second category from review, step S29.

As mentioned above, a reference field may be included, either at least once per stained batch (staining event), or on each glass slide where two or more samples are fixed. This reference field will allow for harmonisation of different staining between the patient sample and the samples used to select threshold and colour range for operations. Thus, an optional step of the method for selection of tissue or cell samples comprising cells belonging to a first category is to include a similarly stained reference field adjacent to each sample or at least on the same sample slide, and using this to adjust colour range using the reference field step S23. According to some embodiments, the adjustment of colour range is performed by comparing the intensity of reference field, step S23*a*.

Also, in some embodiments, step C) comprises the additional step of weighting the pixels based on the distance to red coloured pixels, wherein a weight value is assigned to each remaining pixel, which weight value is based on the distance from the closest remaining red coloured pixel, and wherein a low value is assigned if the pixel is close to the closest red coloured pixel, and a high value if the pixel is far from the red coloured pixel.

Figure 13:
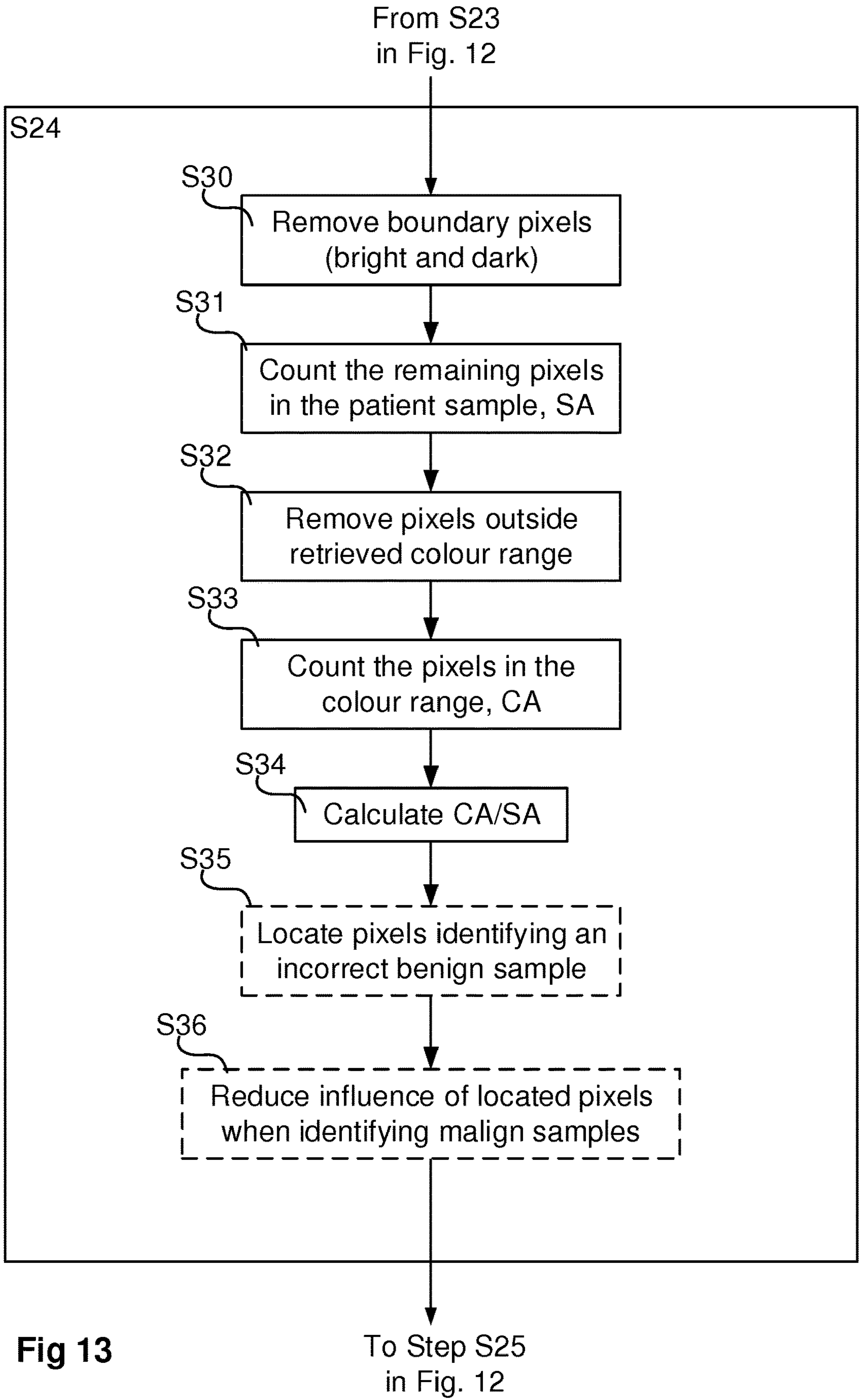
FIG. 13 illustrates a flowchart of further optional steps of a method for selection of tissue or cell samples comprising cells of a specific category.

As mentioned earlier, several samples are often taken from the same patient when assessing for instance prostate cancer, and not every sample may indicate a non-normal sample. Thus, in an optional step all results from samples from the same patient are aggregated, and normal samples are re-classified as non-normal samples if any of the patient samples is classified as non-normal in step C), steps S27 and S28. Further, as illustrated in FIG. 13 and explained in more detail above, step C) is preferably performed by:

C1) removing pixels in sample images corresponding to background area, step S30;

C2) counting the remaining pixels in the sample area, SA, to obtain a total sample pixel count, step S31;

C3) removing the pixels outside the retrieved colour range from the sample image, step S32;

C4) counting the remaining pixels in the colour range, CA, to obtain a pixel count corresponding to colours in cells belonging to the first category, step S33;

C5) optionally removing the pixels outside the red colour range from the sample image; and C6) calculating a total pixel number in the form of a ratio of pixels in the colour range for the sample image by dividing the pixel count corresponding to colours in cells belonging to the first category (CA) by the total sample pixel count (SA), step S34.

In alternative embodiments of the method for selection of tissue or cell samples comprising cells of a first category, the total pixel number is a sum of abnormal pixel weights in the colour range for each patient sample image, or for individual groups in a sample image, based on the grouping of pixels by adjacency (location), such as within one or more groups of pixels. In this way, non-normal cells gathered in blobs, such as cancer blobs, of relevant and/or sufficient size can be identified. For example, this way one large blob of cancer cells and/or several smaller groups, that together have a relevant/sufficient size, can be captured. As an example (see also below), one would say sample belongs to category 1 if any one group has pixel number >=1000 or if the sum (all groups) has a pixel number >=3000. Here 1000 and 3000 are example thresholds for the first and second threshold value, respectively.

According to this embodiment, wherein remaining pixels correspond to pixels within the colour range, step C) may comprise the steps of:

C11) optionally removing pixels in sample images corresponding to background area;

C12) removing the pixels outside retrieved colour range from the sample image;

C13) optionally removing the pixels outside the red colour range from the sample image;

C14) assigning remaining pixels into groups, such that all remaining pixels belonging to the group are within a maximum distance from other remaining pixels in that group, and each group is within a minimum distance away from all remaining pixels not belonging to that group;

C15) calculating the total pixel number for each group as a sum of abnormal pixel weights by summarising all pixel weights of the remaining pixels of that group.

Thus, nearby cancer pixels inevitably end up within the same group and it also explains how new groups are created—by not being able to assign pixels to any existing group if they are more than a maximum distance away from any existing group.

The minimum and maximum distances that are referred to in this embodiment are variable based on weighted-cancer-pixel density and values, Thus, it is not as simple as giving concrete min and max distance values. These distances emerge from blurring the weighted cancer image and then thresholding, as illustrated in Example 4.

By assigning weighted values to all remaining pixels, one or more groups of pixels can be identified. This way, an absolute value (sum of pixel values) is compared to the retrieved threshold value, instead of a relative value (ratio of pixels). By using an absolute value, one or more blobs (groups) of non-normal cells that are sufficiently large can be found, whereas using a relative value, the amount of non-normal cells per sample image is identified.

When identifying more than one group of non-normal cells, at least one predetermined or retrieved threshold values can be used. For example, a first predetermined threshold value can be used to identify smaller groups of pixels that indicate a non-normal sample, and which group of pixels independently would have a sum of pixel values that do not qualify as a non-normal sample. A second threshold value can then be applied for the sum of pixel values for all remaining groups of pixels. Typically, the second threshold value would be on a higher level compared to the first threshold value. In this way, the risk for eliminating non-normal samples from further analysis is limited. Thus, either one predetermined (not retrieved) threshold comparing it to the largest pixel value (the largest group in the image) is used, or alternatively two predetermined thresholds may be used, wherein the smaller one is for the largest pixel value (the largest group) in the image, and the larger one is for the sum of all pixel values (groups) in the image. Moreover, if at least one larger group of pixels indicating non-normal sample (above first threshold value) is found, then there is no need to further test with the second threshold.

But if no such larger group was found, then a second threshold value can additionally be applied for the sum of pixel values for all groups in the image (not excluding any group). The second threshold value would be higher then the first one because the combined pixel-value from all groups needs to be larger to constitute non-normal sample, than the pixel value which is concentrated in just one group.

The values of the first and second threshold values values can e,g, be derived experimentally: if the method of the invention is run on a batch of images where normal and abnormal samples are known, and generate two charts: one for the first threshold, plotting the largest group value (ignoring smaller groups) (Y axis) per each image (X axis is just the image number), and we colour the value points differently for normal and abnormal images, then we can see in the chart where the threshold line should be to separate the normal and abnormal points correctly. The second chart for the second threshold value is similar, with the difference that the sum value from all groups in the image is plotted, instead of just the one largest group per image.

Optionally, it may be included to filter non-normal (cancer) groups by size. This may be performed by discarding groups with size (=width+height) smaller than a chosen limit, such as 175 pixels (corresponds to 320 micrometers). This step is done after grouping, right before comparing values to thresholds.

This size threshold has a different meaning (dimensions) than the first and second threshold discussed above, that may be used on sums of group weights (sum-weight).

Accordingly, the methods of the invention allow for the use of one or more threshold values in order to determine which pixels, or groups of pixels, that are, or contain, pixels indicating a non-normal or normal sample, i.e. belonging to the first or second category of samples. Each thereshold is either retrieved (e.g. obtained from a previous calculation), or predetermined (provided by the user(s) of the methods). Thus, in some embodiments, a first threshold is compared to each group of pixels in a sample image, and/or a second threshold is compared to the sum of all groups of pixels in a sample image, and/or a third threshold is compared to the size of a group of pixels in a sample image.

As described above, if any colour ranges are known to interfere with the classification of samples, such as the brown periphery of blood in a prostate sample, this colour range may be located and the influence of these and nearby pixels may be decreased in the calculation of the ratio. Thus, further to step C5 or C15 above, as is exemplified in connection to FIGS. 5 to 9 above, the following steps may be applied;

locating pixels in a pre-determined exclusion colour range, EA, step S35;

reducing the influence of said located pixels in step C4) (or step C14) when counting the remaining pixels in the sample image, to obtain a pixel count corresponding to colours in cells belonging to the first category (CA), step S36.

Examples of an exclusion area, EA: presence of blood in sample, red colour being close to colour range identifying normal (healthy) cells.

The reason for this is that red colour indicates blood and thus healthy cells. Lack of red colour increases the chances of non-healthy cells. Typically, healthy cells should have some red colour.

In the optimisation of the method, one searches for cancer (brown) colour and optionally also for blood (red) colour. Then the weights of cancer pixels closest to red colour pixels are reduced (optional step), in order to diminish the impact of those cancer colour pixels because they are less likely to be cancer for being near blood.

One additional reason is also that red colour is basically dark brown colour, but they have opposite meanings: typically, blood means that the cell is healthy, brown means the presence of cancer. Yet these colors may be difficult to separate and some red (blood) pixels get wrongly detected as cancer pixels. But then because they are also surrounded by neighbouring red (blood) colour pixels, these false detections get zero weights and will not affect results.

Also, according to some embodiments of the methods, step C) comprises the additional step of weighting the pixels based on the distance to red coloured pixels, wherein a weight value is assigned to each remaining pixel, which weight value is based on the distance from the closest red coloured pixel, wherein a low value is assigned if the pixel is close to the closest red coloured pixel, and a high value is assigned if the pixel is far from the red coloured pixel.

In the above method for defining a colour range, after classifying or dividing the samples into two different categories, a sample image is obtained of each sample. This may be done using an image scanner of a suitable type.

In yet another embodiment, described in further detail in example 5, the invention refers to a method for selection of tissue or cell samples as disclosed above wherein after step B and before step C, edges of the sample image are cut off, in order to reduce the risk for samples being falsely classified as belonging to the first category.

Figure 14:
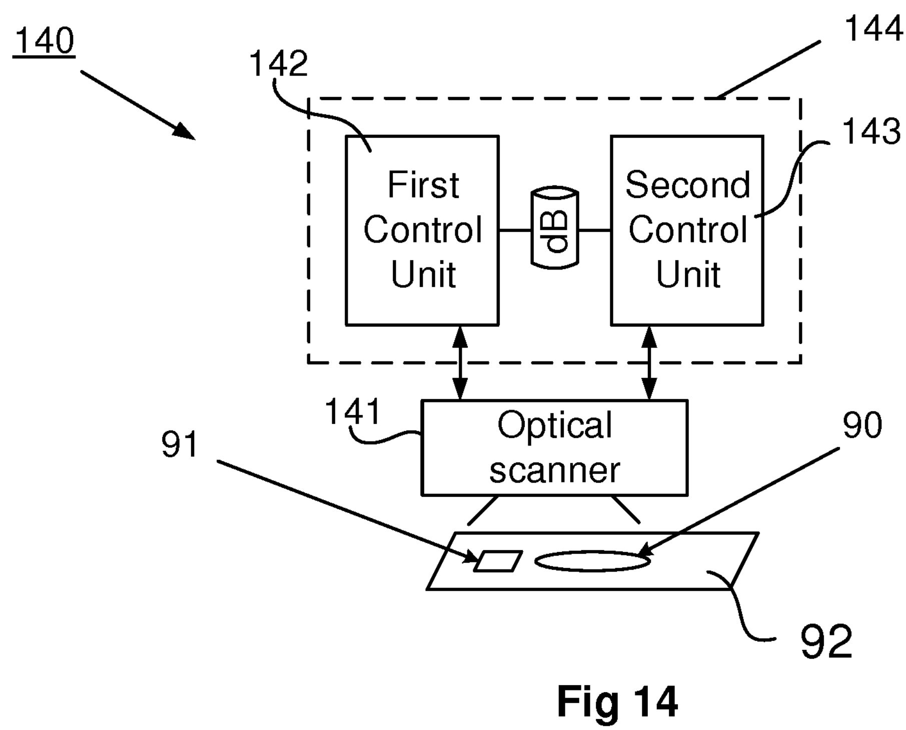
FIG. 14 illustrates a system for calibration and/or operation of a method for selection of tissue or cell samples comprising cells of a specific category.

FIG. 14 shows a system 140 for defining a colour range for use when identifying presence of cells belonging to a first category in a tissue or cell sample using a plurality of samples 90 divided into at least one batch, each batch being stained and each sample being classified into a first and a second category. The system 140 comprising an image scanner 141 configured to obtain a sample image of each sample 90, a first control unit 142 and a data storage unit dB. The first control unit 142 is configured to:

define a colour range for each batch of sample images identifying samples belonging to the first category;

evaluate the sample images in each test batch and adjusting the colour range for each test batch to ensure all samples belonging to the first category is correctly categorized; and store the adjusted colour range for use when identifying cells belonging to the first category in a tissue or cell sample in the data storage, dB.

FIG. 14 also shows a system 140 for selection of tissue or cell samples comprising cells belonging to the first category, using at least one patient sample 90 comprising tissue and/or cells being stained, the system comprising an image scanner 141 configured to obtain a sample image of each patient sample 90, a second control unit 143 and a data storage unit dB. The second control unit 143 is configured to:

retrieve a colour range from the data storage unit dB, the colour range being determined by a system as described above;

determine a total pixel number, such as a sum of abnormal pixel weights or a ratio of pixels CA/SA in the colour range for each patient sample image;

classify each patient sample as belonging to the second category if the total pixel number in the sample image, or per group in the image, depending on which threshold(s) the total pixel number is compared to and which embodiment is used, is below one or more predetermined threshold(s), or classifying each patient sample as belonging to the first category if the total pixel number in the sample image, or per group in the image, depending on which threshold(s) the total pixel number is compared to and which embodiment is used, is above or equal to the threshold(s); and identify patient samples belonging to the second category to be removed from review.

The first control unit 142 for defining a colour range may also be used to regularly calibrate the system in order to detect and adjust variations in the image scanner. Furthermore, the first control unit 142 and the second control unit 143 may be implemented in a system with an integrated database for storing data, as indicated by the dashed line 144 in FIG. 14.

A sample carrier 92, upon which one or more samples 90 are provided, may also be provided with a reference field 91 used for adjust colour range as described above.

Figure 15:
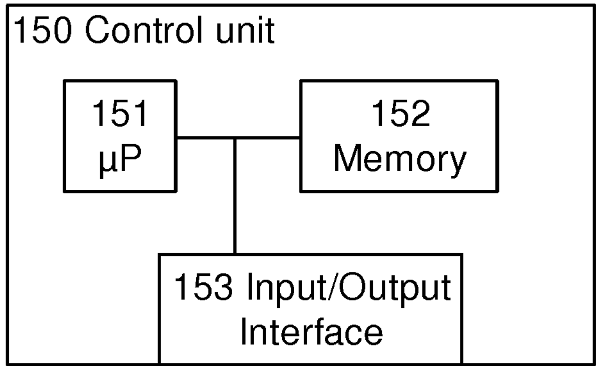
FIG. 15 illustrates a control unit configured to execute software in order to perform the methods described herein.

FIG. 15 shows a generic control unit 150 suitable to implement in the system described in connection with FIG. 14. The control unit 150 comprises a processor 151, a memory 152 and an input/output interface 153. The processor is configured to execute instructions, which may be stored in the memory 152, and communicate with external units (such as an optical image scanner 141 and data storage dB) via the input/output interface 153.

The methods described in connection with FIG. 11 may be implemented in a computer program for defining a colour range for use when identifying presence of cells belonging to a first category in a tissue or cell sample, comprising instructions which, when executed on at least one processor 151, cause the at least one processor 151 to carry out a method according to the method described in connection with FIG. 11.

Figure 16:
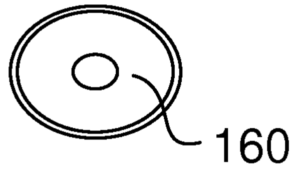
FIG. 16 illustrates an exemplary apparatus configured to carry the software configured to perform the methods described herein.

FIG. 16 illustrates a computer-readable storage medium 160 for carrying a computer program for reconstructing events related to defining a colour range according to the method described in connection with FIG. 11 and/or for selection of tissue or cell samples comprising cells belonging to a first category according to the method described in connection of FIGS. 12 and 13.

The methods described in connection with FIGS. 12 and 13 may be implemented in a computer program for selection of tissue or cell samples comprising cells belonging to a first category, comprising instructions which, when executed on at least one processor 151, cause the at least one processor 151 to carry out a method according to the method described in connection with FIGS. 12 and 13.

EXAMPLES

Example 1

Needle biopsies (1.0 mm in diameter, core biopsies) of prostatic gland tissue are fixed in 10% neutral buffered formalin and paraffin embedded and sectioned in about 4 μm thin sections. The stained sections are immuno-stained with tree different antibodies: P504S (AMACR), p63 and CK5 (cytokeratin 5).

The prostatic gland is built up of a glandular epithelium surrounded by connective tissue. In the periphery of the glands myo-epithelial cells are located. The myo-epithelial cells are immune-histochemically stained with p63 and CK5 antibodies, whereas the glandular epithelial cells are unstained. The P504S antibody stain epithelial cells transformed to adenocarcinoma, whereas myo-epitelial cells and normal glandular cells are unstained. Consequently: in prostatic adenocarcinoma the glandular cells are immuno-stained with P504S (brown staining) and the peripheral myo-epitelial cells has disappeared. In normal prostatic glands the glandular cells are unstained and the peripheral myo-epithelial cells are immuno-stained with antibodies to p63 and CK5 (red staining). Thus, the staining pattern using immuno-histochemistry (antibodies to P504S, p63 and CK5) the two colours employed, brown and red, is fundamentally different in normal prostatic gland and in prostatic adenocarcinoma. Hematoxylin-eosin is used as a background staining (light blue) of the tissue sections.

Example 2

Tissue from lymph nodes were fixed in 10 percent neutral buffered formalin and embedded in paraffin. Thin sections, 4 μm, were cut and placed on glass slides. After dehydration in graded alcohols, the sections were immune-stained with antibodies to an epithelial cell marker BEREP4, which binds to normal epithelial cells and epithelial derived cancer such as colon cancer. The BEREP4 antibodies were visualised by a brown staining with DAB (diaminobenzidine) as chromogen. Hematoxylin was used as a background staining of the lymph node tissue, by giving a light blue staining of normal lymph nodes. After that the sections were coated with a glass cover.

Normal lymph nodes lack epithelial cells and are unstained with the BEREP4 antibodies whereas lymph nodes with metastases from colon cancer contain cells to which the BEREP4 antibodies are attached. Thus, a brown staining is present in addition to the light blue background staining used to visualise the sections in the microscope image. All regional nymph nodes in patients with colon cancer are analysed to identify which lymph nodes are normal and which contain metastatic cancer.

The BEREP4 antibody stains glandular cells of normal colon and is used as a positive control of the staining.

Example 3

Two examples of preparation of a reference field sample is as follows. Human kidney cells are fixed and sectioned as described above or commonly known in the field. These samples are immunostained with P504S (AMACR) and used as reference fields in the assessment of prostate gland samples. Similarly, human epithelial cells are fixed and sectioned as commonly known, and immunostained with p63 and CK5 (cytokeratin 5) and used as a reference fields for prostate gland samples.

Example 4—Cancer Grouping Into Blobs for Absolute Valuation Program Flow

1. Input Data

First, cancer colour is filtered the same way as described above, i.e. define cancer and blood colours, then filter the image leaving only cancer colour (as binary image, 1 where cancer colour, 0 rest), then filter the image leaving blood colour and use it to make a distance transform image (pixel values 0 to 255 inversely proportional to distance from blood), then multiply the cancer image with the distance transform image to get cancer image weighted for distance to blood.

Figure 17:
Figure 18:
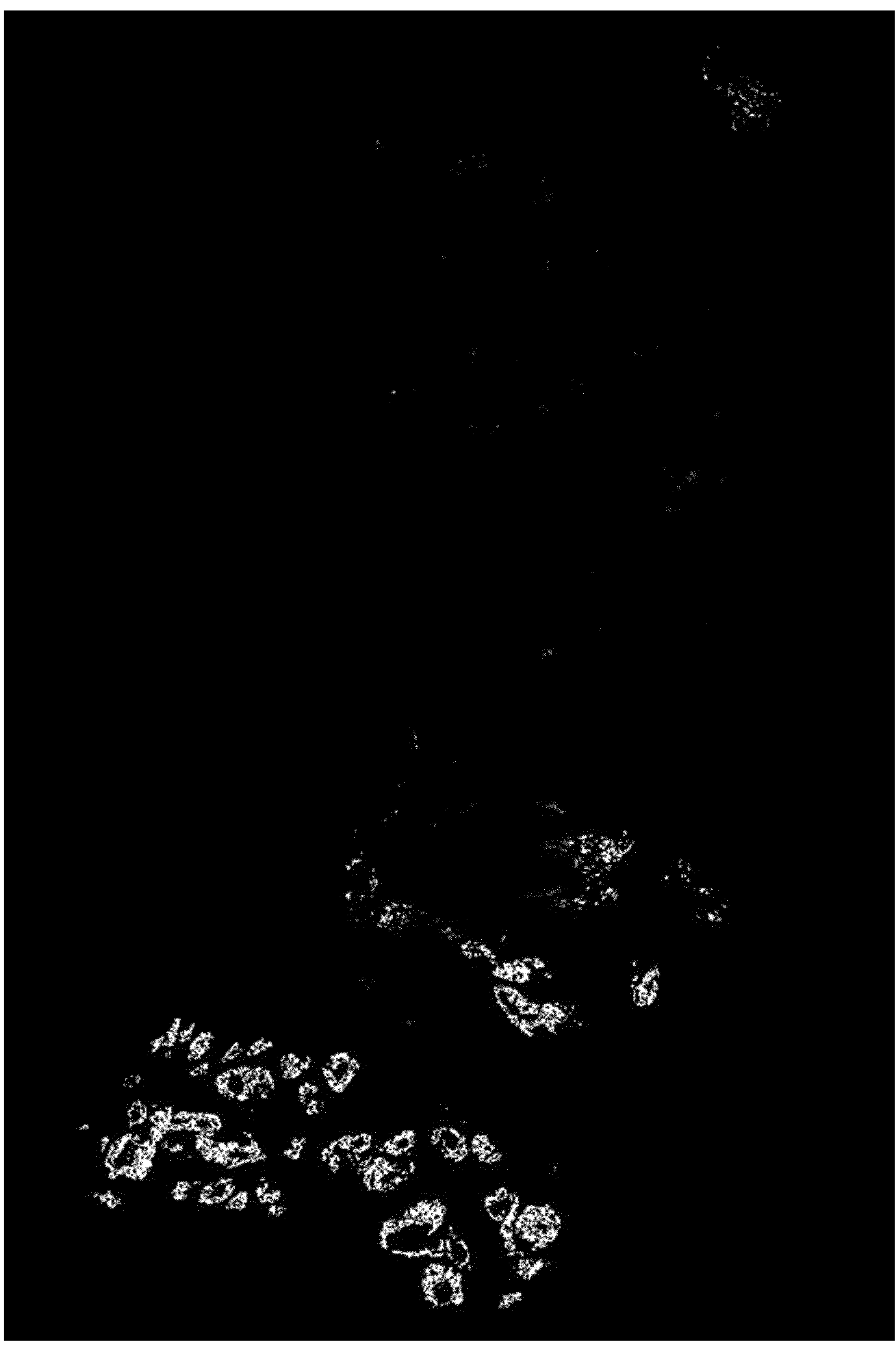
Figure 19:
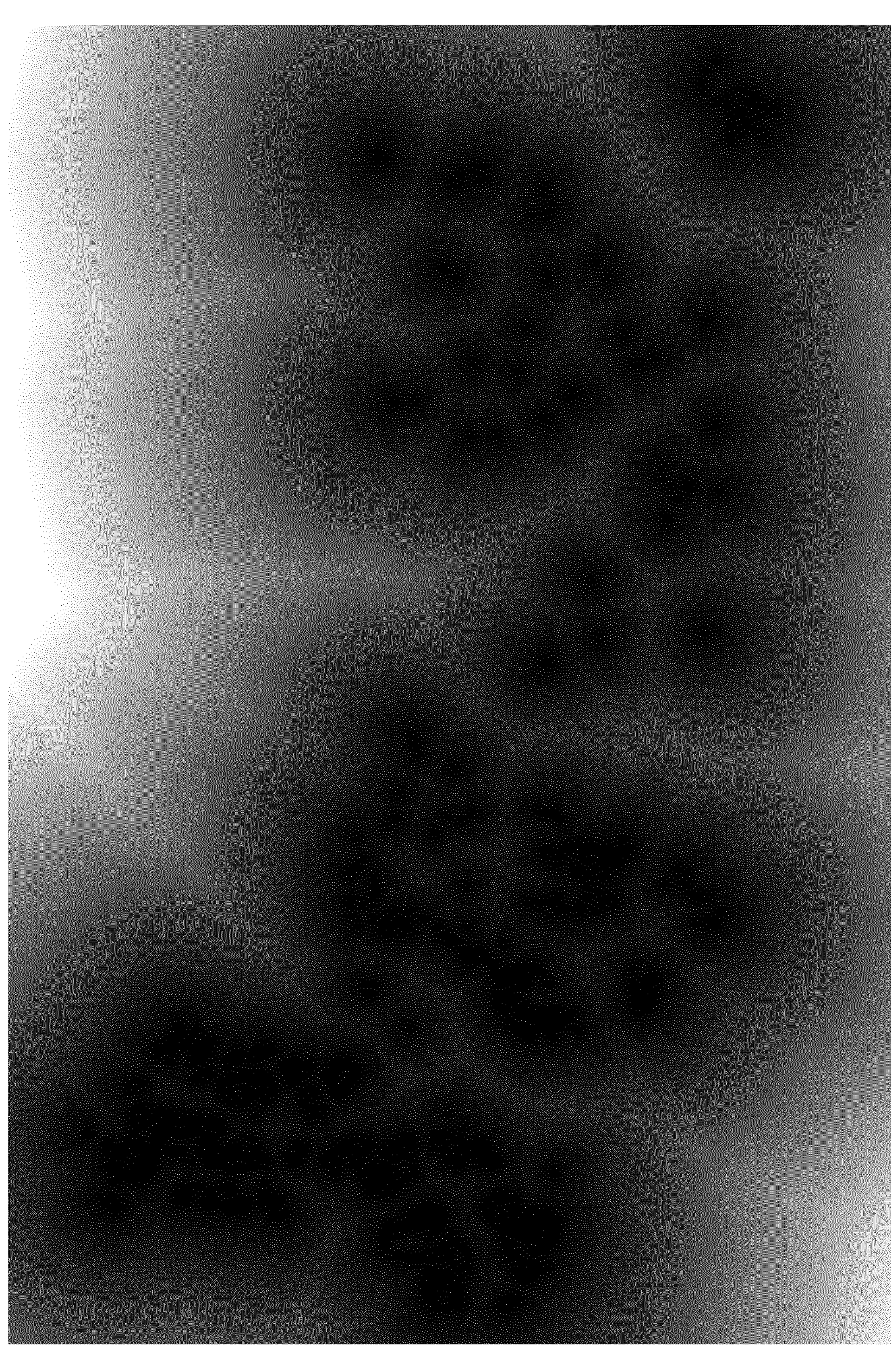

FIG. 17 is the source image, and the weighted cancer colour image is FIG. 18. The weighted cancer image (FIG. 18) will be the input for grouping.

Note that optional additional steps such as finding sample edges and cutting of some of them may be used to reduce false positives from the connecting tissue. These steps are covered in Example 5.

2. Grouping of Cancer Pixels

First, one needs to find a way to evaluate the distance between white pixels in the weighted cancer image. Two ways may be used: one is to use a distance transform and then threshold it, the threshold value being the desired grouping distance (in pixels) divided by 2. Another way is to blur the weighted cancer image using blur element size equal to the maximum desired grouping distance +1, and then threshold that with the threshold value of 0. For now, the second method is used.

2.1. First Method

Figure 20:
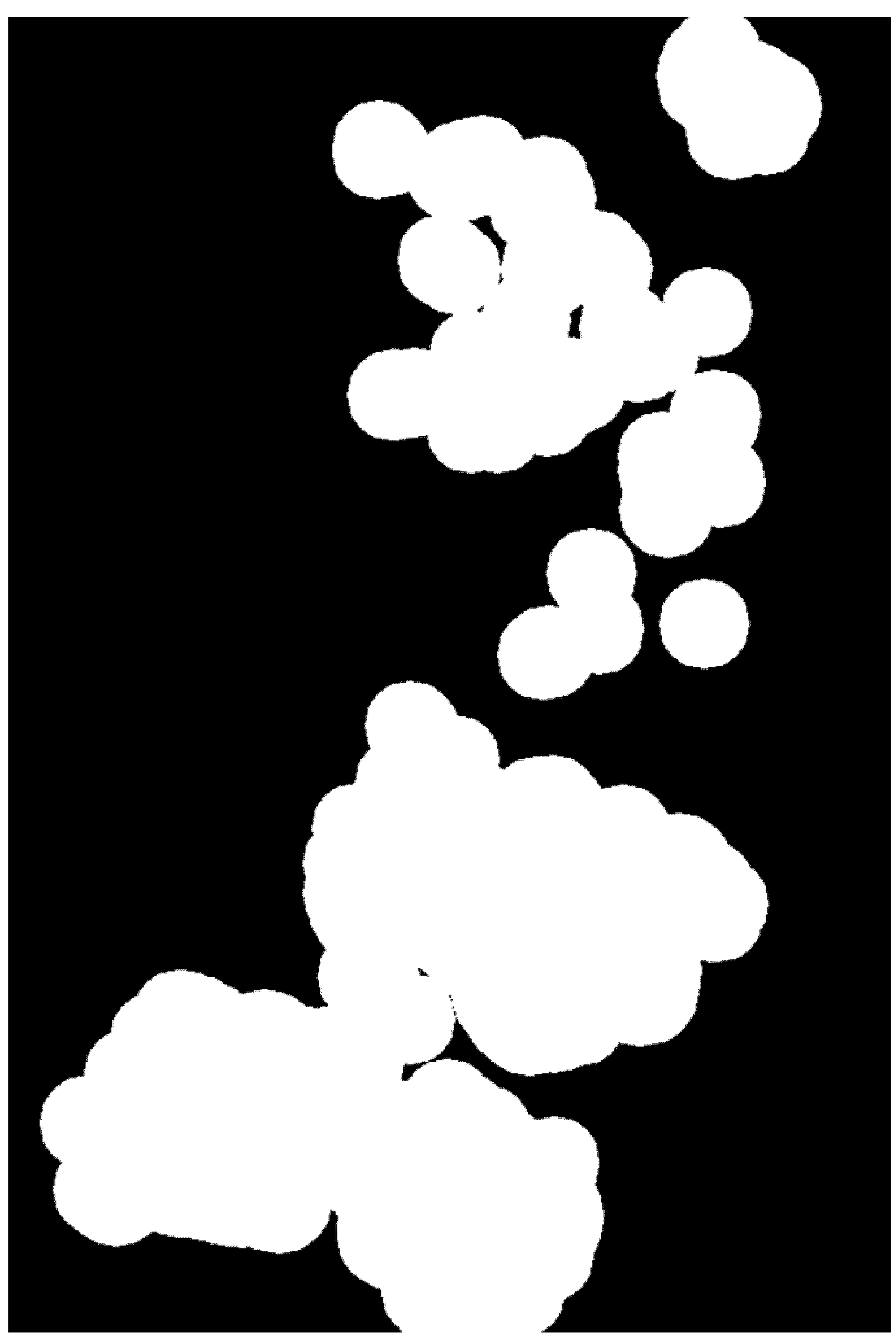
Figure 21:
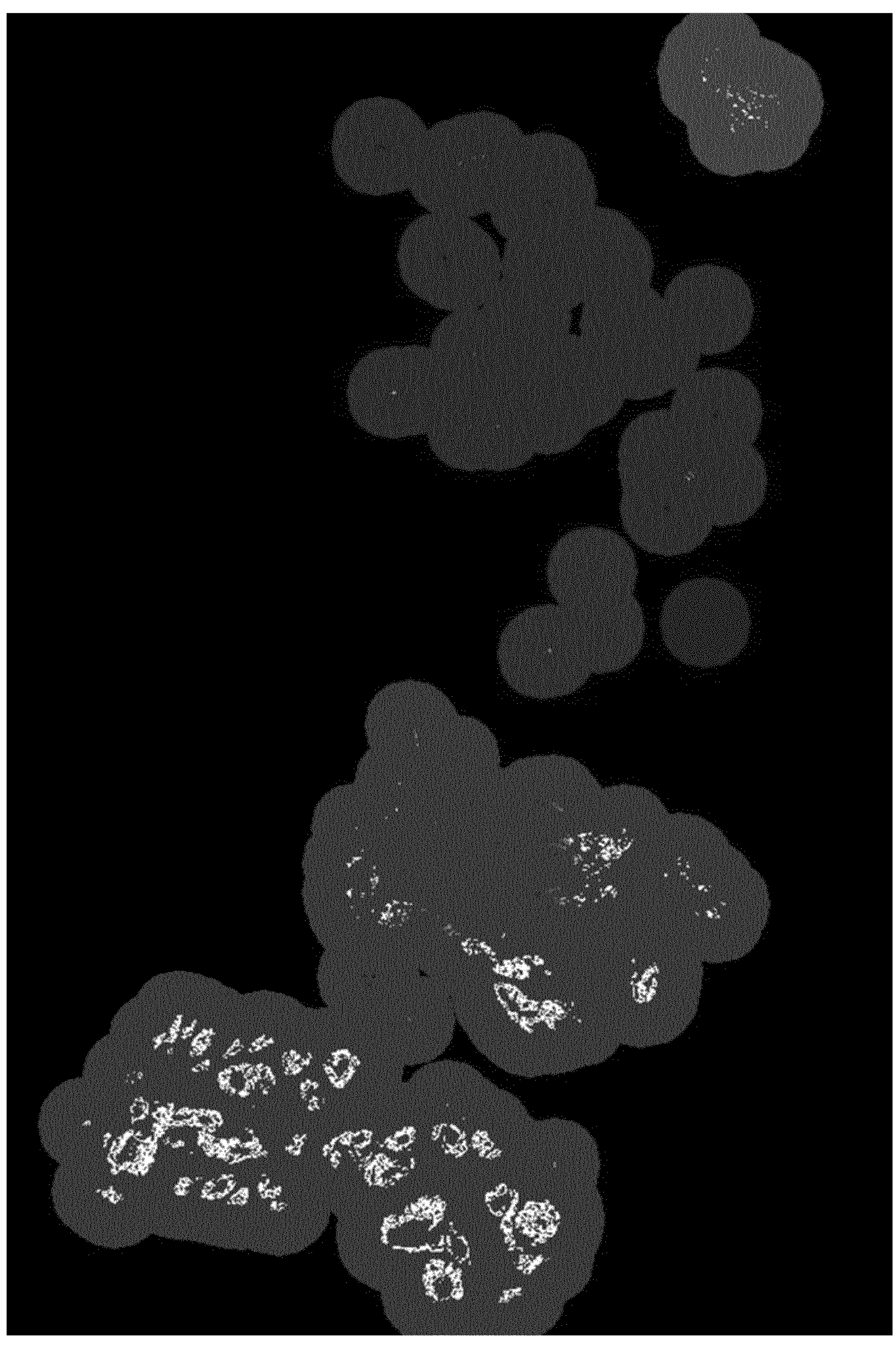
Figure 22:
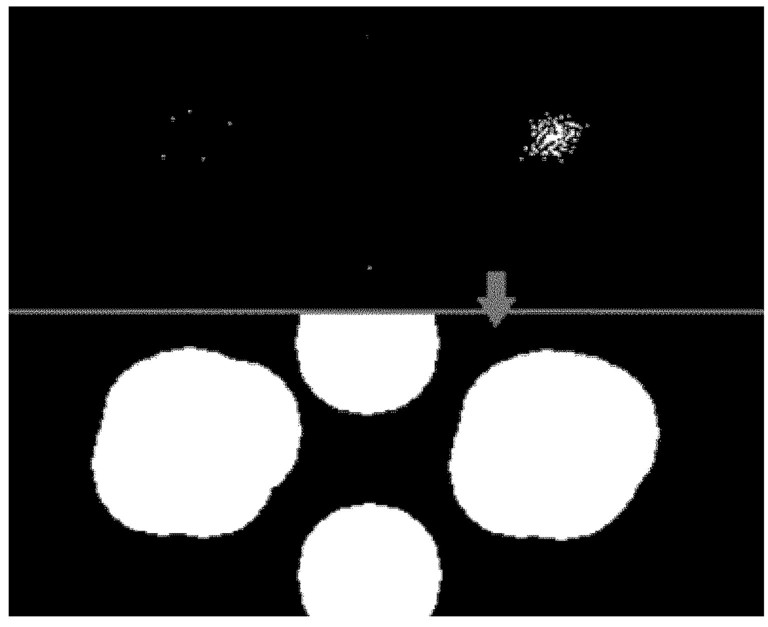

To start with, the first method is illustrated because it is simpler to understand and will also help understand the second method easier. If one wants to group cancer pixels over maximum distance of 60 pixels: see next the images of the "cancer image after distance transform" (FIG. 19) and that "distance transform thresholded with value 30 (=distance/2) and inverted" (FIG. 20). (Inverted =white becomes black and vice versus):

As can be seen, all white pixels became white circles with radius 30, then the circles from white pixels that were closer than 60 pixels apart will overlap, resulting in composite larger blobs.

The next step would be to sum the values of all cancer pixels covered by one blob (and do so for every blob).

In the next image (FIG. 21) the different blob coverages of cancer pixels are illustrated with unique colour for each blob and one can also see the weighted cancer pixels (white) belonging to each blob. It is just an illustration that was made to help understand. No coloured blob images are used in the program.

Also keep in mind that the blobs are used only to group the pixels. Cancer activation calculation for each group is done by summing the values of pixels in the weighted cancer image (FIG. 18) that are located in the area covered by that blob, as opposed to summing the blob-image pixels. Remember the term "group cancer activation", which term will be used later.

This method is the simpler one as the grouping distance is not affected by pixel brightness (pixels brightness depends on distance to blood), or by neighboring pixels, but each pixel causes a circle of radius always =30. Note however that after the grouping, the pixel brightness will still affect the group cancer activation for that blob, since this value is calculated by summing the weighted cancer pixel values.

2.2 Second Method

The first method had disadvantages that a single random brown pixel (typically noise) located between 2 blobs could end up bridging them over quite a large distance.

Another disadvantage was that there would be no difference in bridging distance between sparse groups of a few pixels and very dense groups (see FIG. 22):

The next method using blurring has unique characteristics:

1) Darker pixels (closer to blood) will cause smaller circles (intrinsic property of blurring itself).

2) A number of very-close-by white pixels will cause a much larger blob than a single pixel of exact same brightness, and denser groups will cause larger blobs than sparse groups (again intrinsic property of blurring itself).

Both these properties are considered desirable and closer to the opinion of the inventors of how pixels should be grouped.

Figure 23:
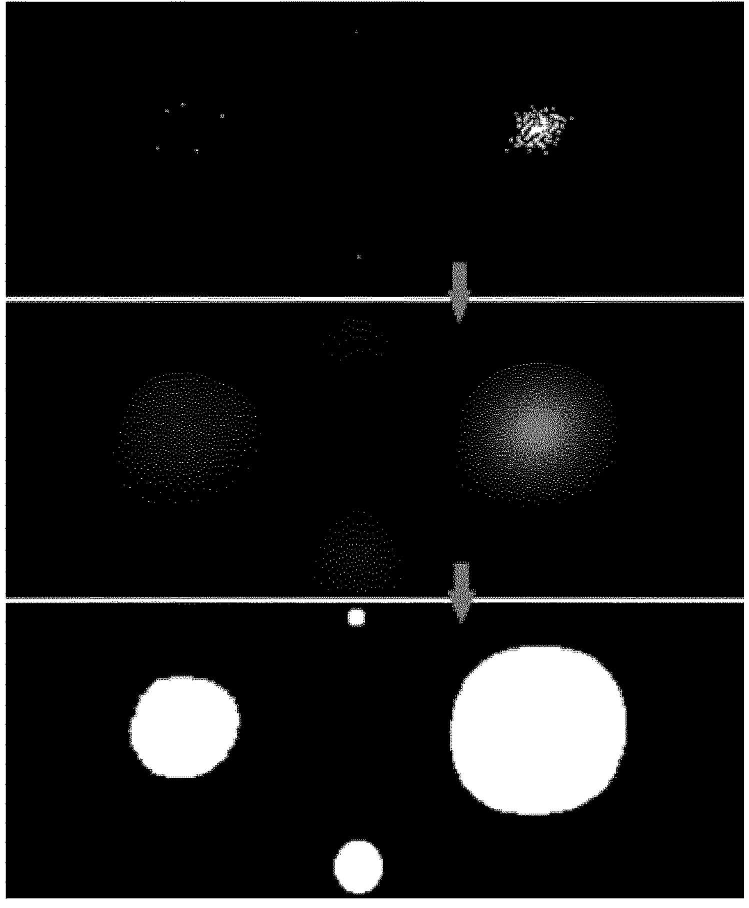
Figure 24:
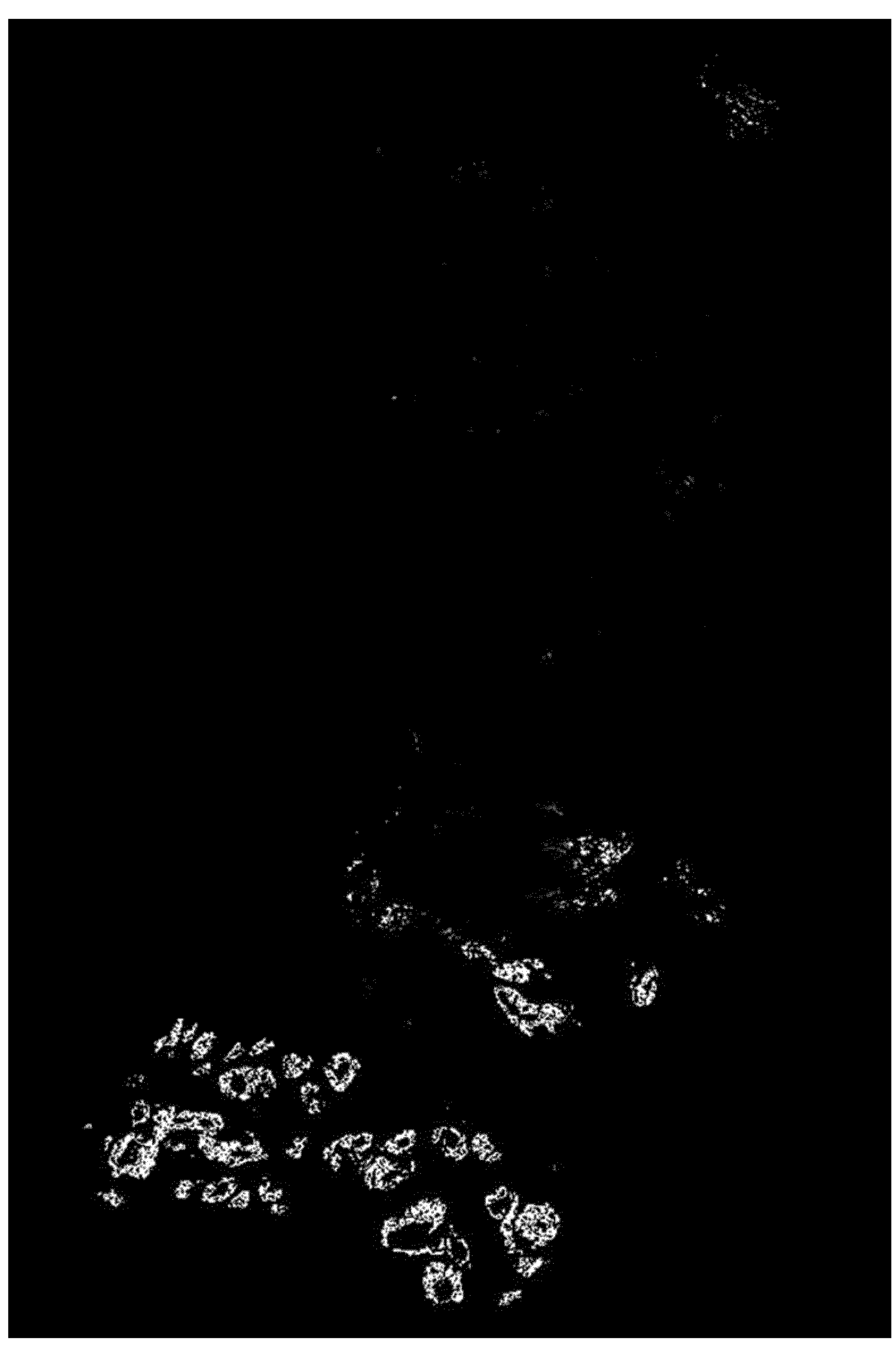
Figure 25:
Figure 26:
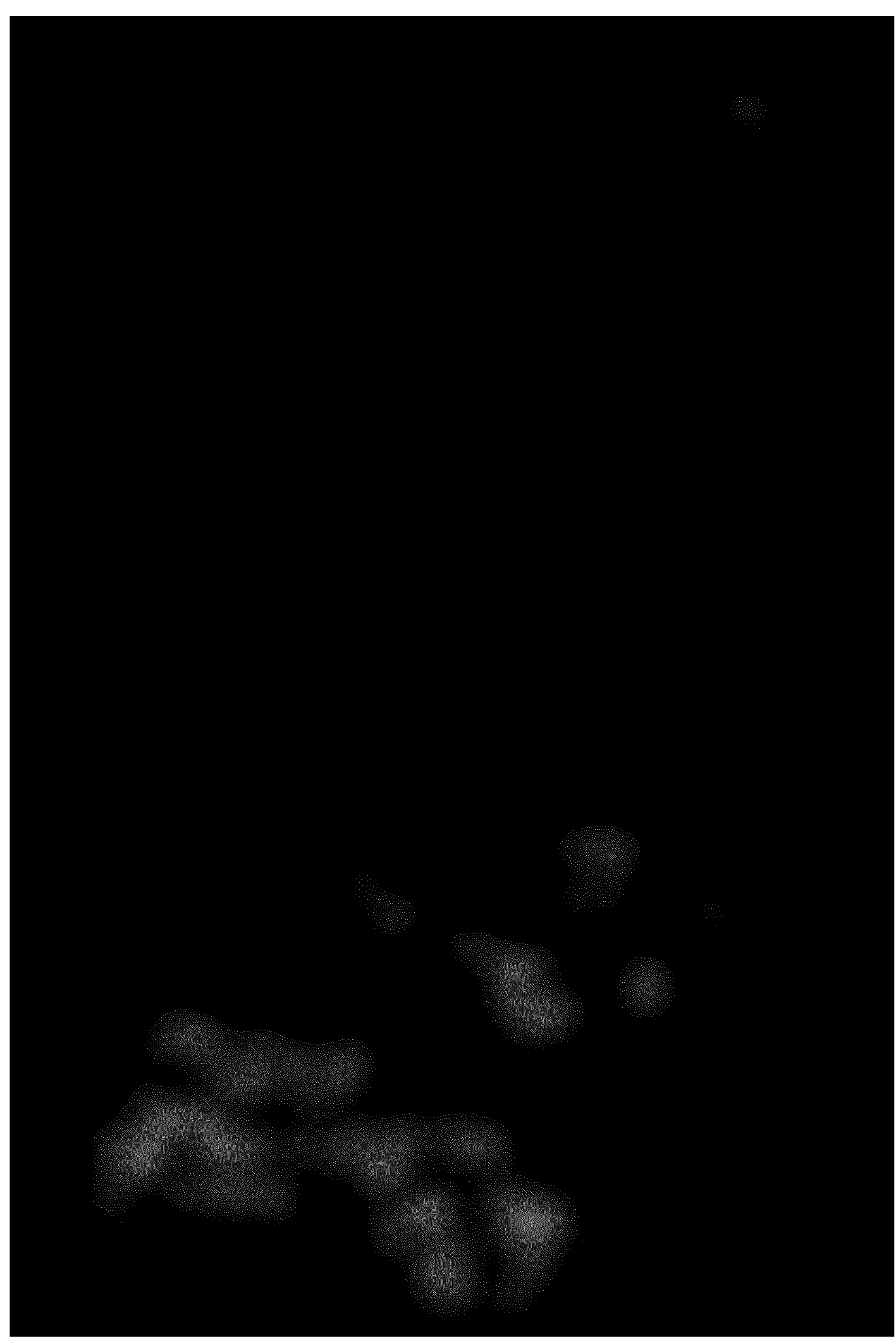

To explain what blurring does instead, see FIG. 23:

Blurring sort of diffuses (spreads) the pixel values over a larger area. If the pixel is whiter, its value can be diffused wider before it completely diminishes. If there are a lot of neighbor white pixels, their diffusion areas overlap, and they support each other by diffusing their white over the neighbor pixel white. For an alternative explanation, search for the term "Gaussian blurring".

Thresholding the blurred image will therefore result in different blobs than the inverted threshold of the distance transform.

Figure 27:
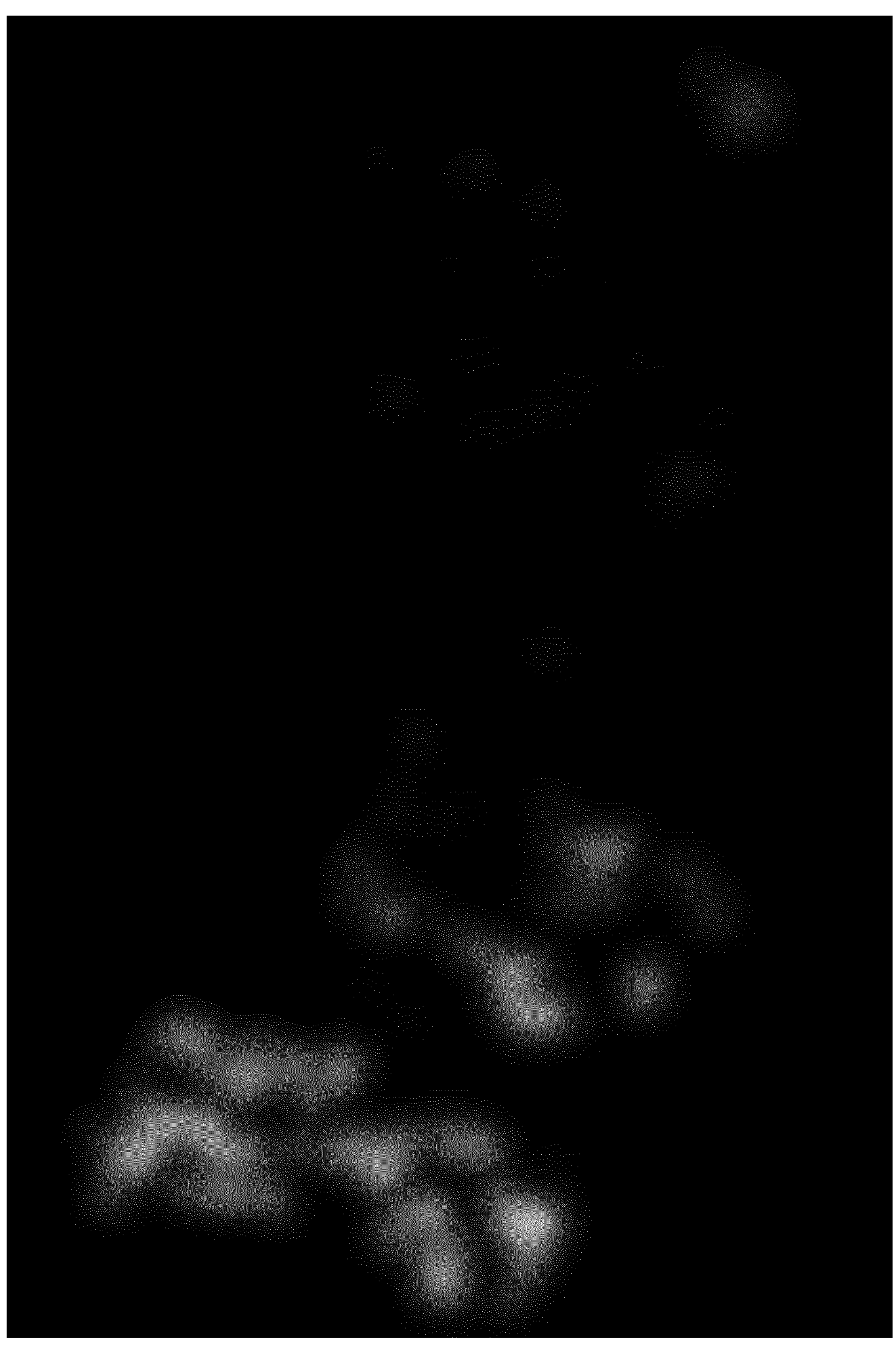

A final note: since pixels are to be connected over very large distances, blurring must be made strongly (diffuse the pixel values over a very large area) and that can cause for alone pixel (especially a darker pixel) to get so diffused that even its maximum value at the center becomes zero. In other words, when blurring strongly, it is possible for pixels to entirely disappear, especially if a darker pixel and unsupported by nearby neighbors. This effect can be diminished or balanced to ones preference by dilating the weighted cancer image right before blurring (dark pixels far from any supporting neighbors are likely to be noise, so why not let them disappear). Dilating expands every pixel in every direction without reducing its value (one can think of it as enlarging). See FIGS. 24-27: first original weighted cancer image (FIG. 24), then the same image dilated (FIG. 25), then the original (not dilated) weighted cancer image blurred (FIG. 26), then the dilated image blurred (brighter and spreads further)(FIG. 27).

3. Thresholds and Filtering

Now pixel groups have been formed and it must be decided what to do with them, meaning how to decide which groups if any are real cancer.

One may experimentally decide a threshold for "group cancer activation", classifying every group with activation above this threshold as real cancer.

One may have a second, higher threshold for the summed-up activations from all groups "total-image activation".

Additionally one may remove groups that have too small area.

Example 5—Sample edge cutoff program flow

1. Premisse

The need to remove boundaries arose from an observation that most false detections and trash (connecting tissue, etc.) that has cancer-colour, occur near the boundary.

So, one simply cuts off some of the edge. This will greatly reduce false positives.

NOTE: The amount of cutoff and the usefulness itself are specific to the application of the method to prostate cancer analysis and the used zoom level in the images (roughly 546 pixels per millimeter).

See next the steps one uses to do that:

The resulting removal is on average 14 pixels wide (from every side), which corresponds roughly to 25.5 micrometers at the used zoom level (roughly 546 pixels per millimeter).

Figure 28:

FIG. 28 represents the example source image.

Figure 29:
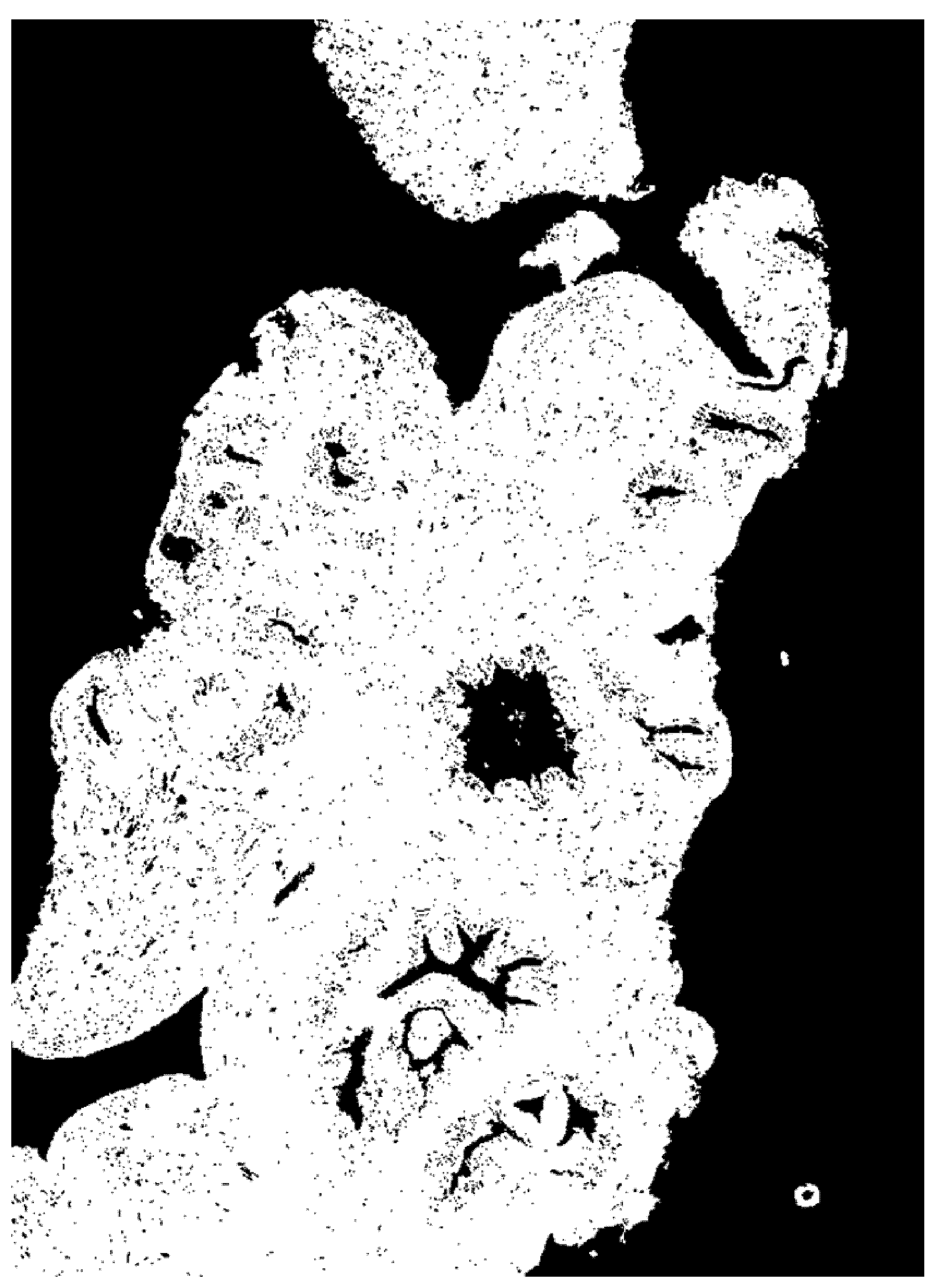

Step 1: Find the edge (just threshold with value 205) producing a binary image (0 and 255) called "mask" (FIG. 29).

Figure 30:

Step 2: Fill all the gaps (one will want to only cut off outer edge in the next step. Filling gaps results in no inner edges) (FIG. 30).

Figure 31:

Step 3: Apply Gaussian blur with element size 17 (FIG. 31).

Figure 32:

Step 4: Apply threshold (use value 254). This removed on average 7 pixels from all sides of the outer edge (~13 um) (FIG. 32).

Figure 33:
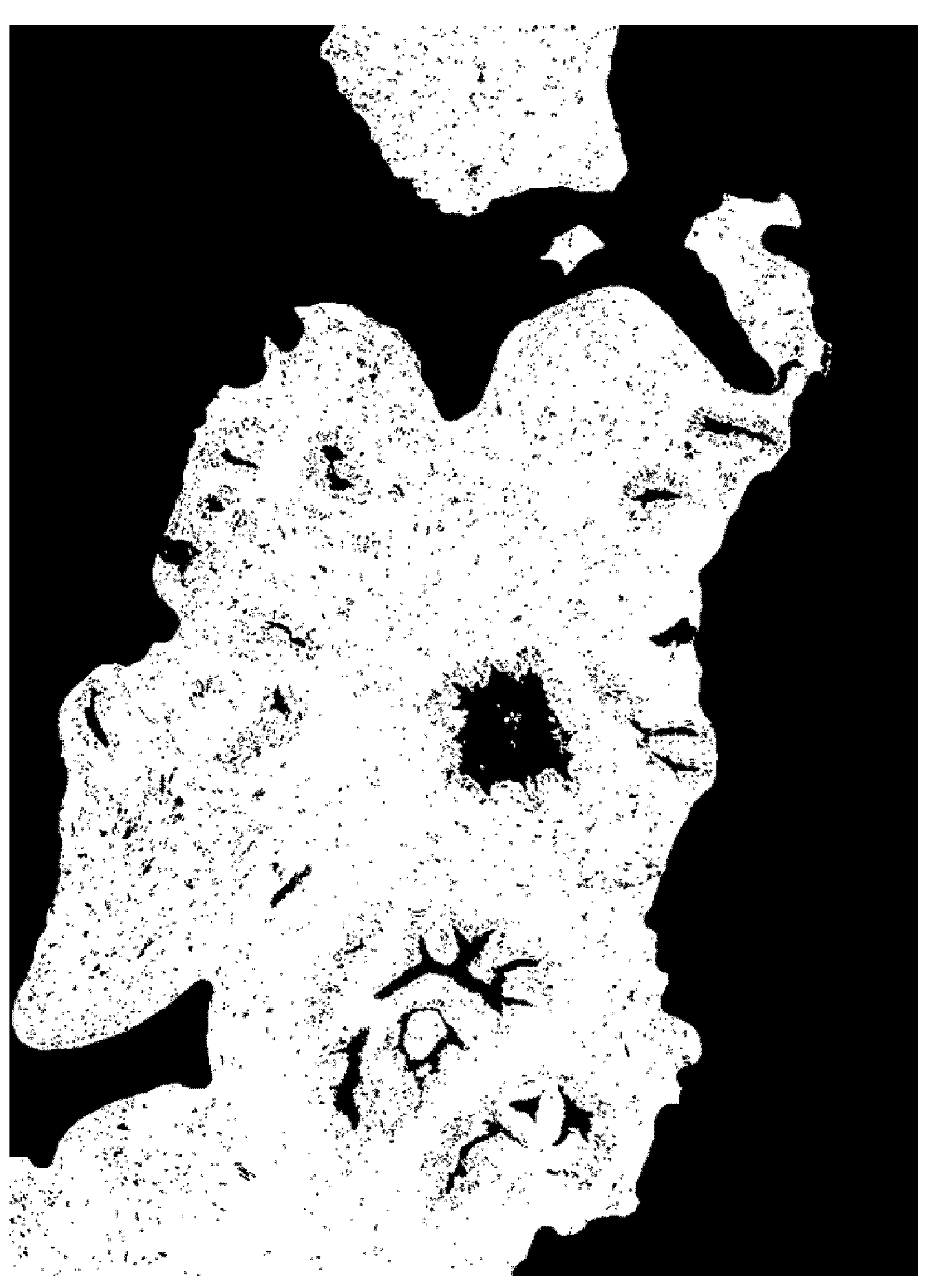

Step 5: Combine the result from step 4 with the result from step 1 (bitwise "and" operation) to restore internal gaps while maintaining the external edge cutoff (FIG. 33).

Figure 34:

Step 6: Blur again with element size 5 and threshold with value 255. This will fill the smallest internal gaps but leave the larger ones not fully filled. All sides will be expanded by 2 pixels (FIG. 34).

Figure 35:

Step 7: Blur with element size 25 and threshold with value 254. This will cut off all remaining edges (internal and external) by additional 9.5 pixels (17 um) (FIG. 35).

Figure 36:
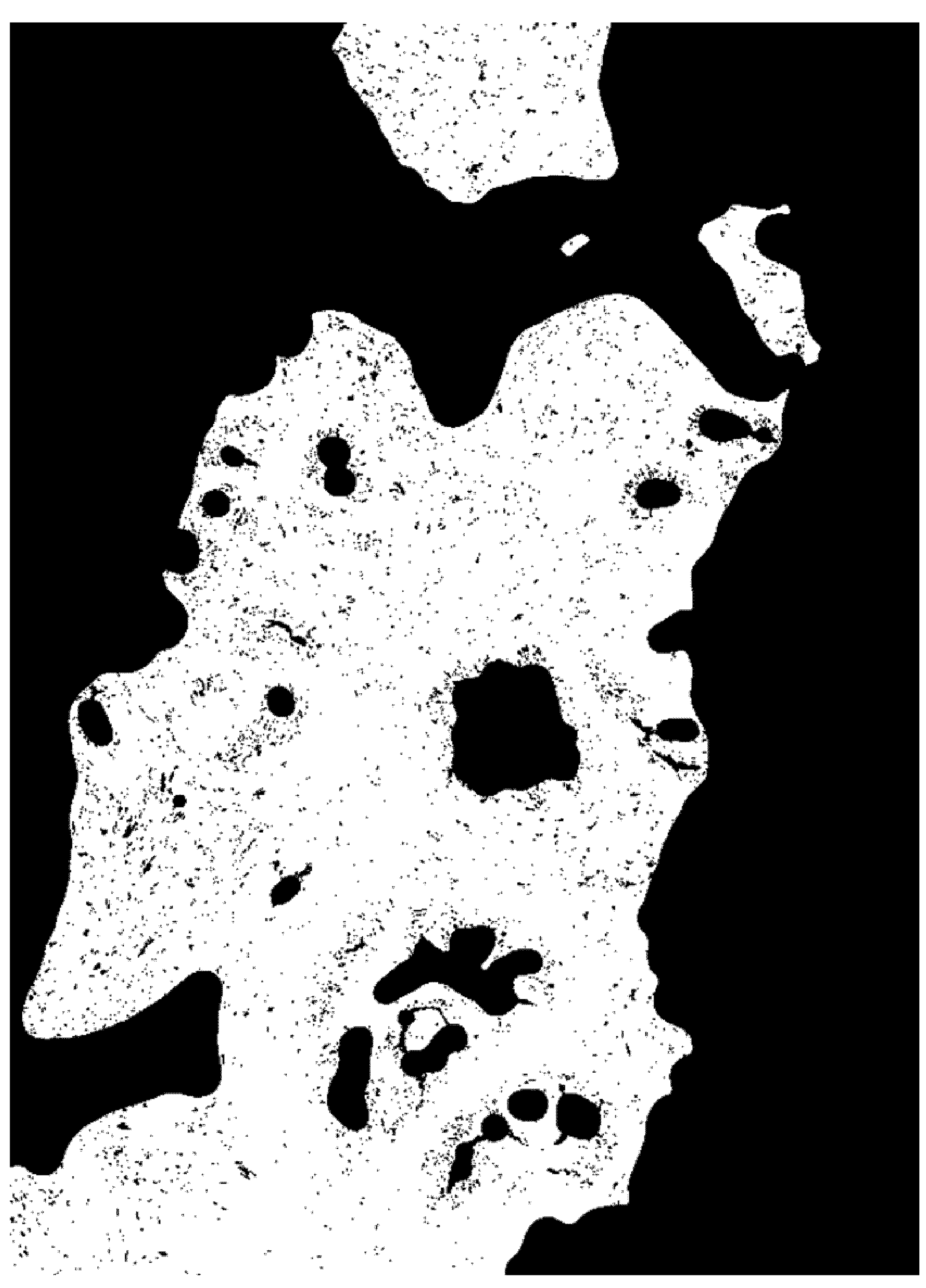

Step 8: Combine result from step 7 with result from step 1 (bitwise "and" operation) to restore small internal gaps. The result from this step is the final mask (FIG. 36).

Figure 37:
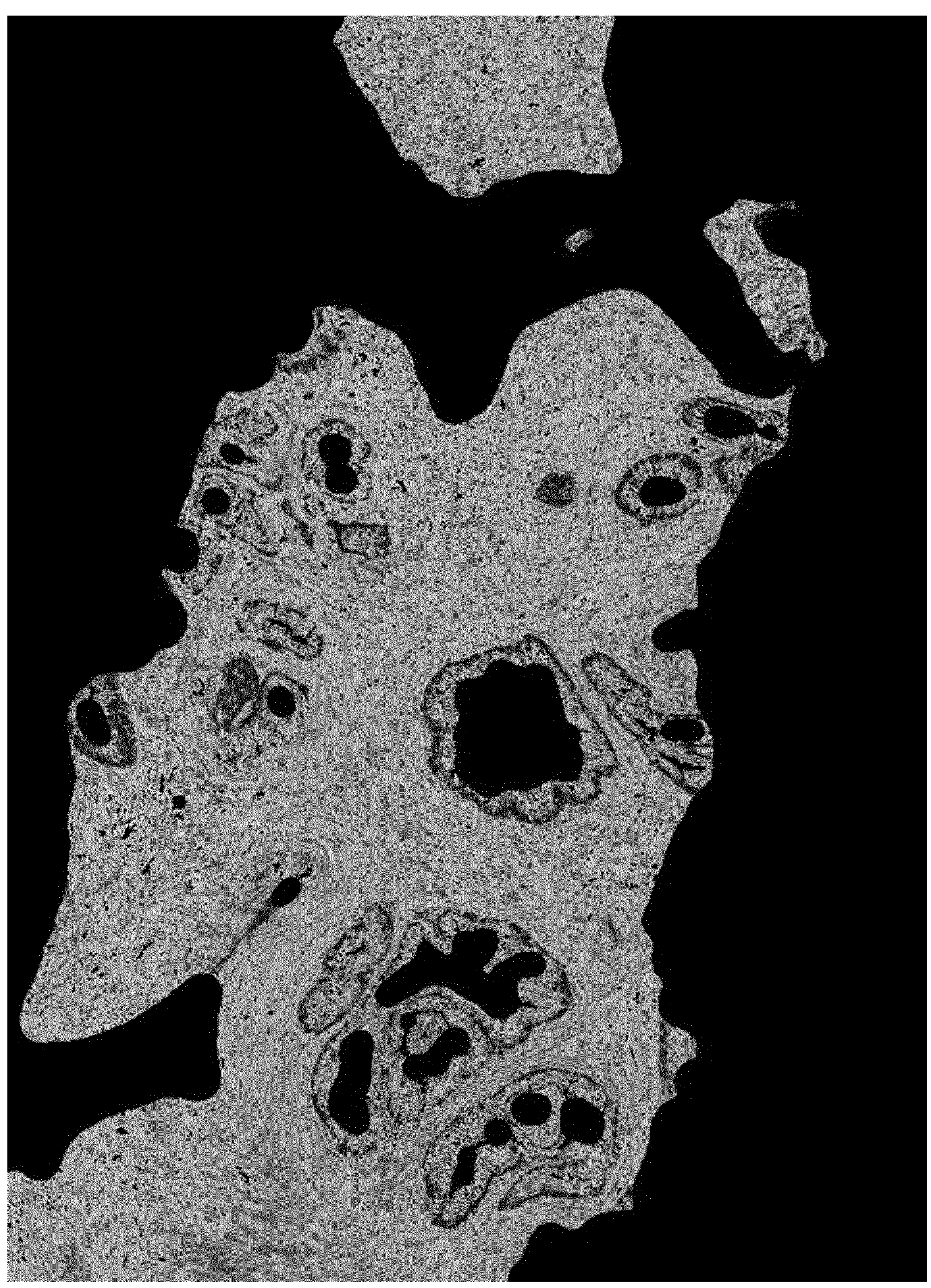

The final mask can be applied to the input image. The combined outer edge removal is on average 14.5 pixels (27 um), and inner edge removal (only larger gaps) 7.5 pixels (14 um) (FIG. 37).

CONCLUDING COMMENTS

The present invention is not limited to the above-described preferred embodiments. Various alternatives, modifications and equivalents may be used. Therefore, the above embodiments should not be taken as limiting the scope of the invention, which is defined by the appending claims.

The inventio claimed is:

1. A method for selection of tissue or cell samples comprising cells of a first category, said method comprises retrieving or predetermining an at least one threshold and a color range determined according to a first set of steps, the color range and the least one threshold for use when identifying a presence of cells of different categories in a tissue or cell sample, wherein the first set of steps comprises:

a) dividing samples into at least two batches, and for each batch staining and classifying each sample into a first and a second category, wherein the samples are pre-classified and/or the classification of samples is performed by medically trained personnel, who will assess each of the samples and categorize it as one of two categories, based on different colorings of the categories, and wherein the first and the second category represent non-normal and normal cell samples, respectively, such as malign and benign samples, or different stages of a disease, such as cancer;

b) obtaining a first set of sample images of each of the samples;

c) defining the color range belonging to a first category for the first set of sample images;

d) evaluating the first set of sample images and adjusting the color range for the first set of sample images, by excluding color values seen in a second category of samples, to ensure all samples in the first set of sample images belong to the first category and are correctly categorized to the first category; and e) selecting the at least one threshold and storing an adjusted color range for use in a second set of steps when identifying cells belonging to the first category in the tissue or the cell sample, wherein the second set of steps further comprises:

A) staining an at least one patient sample comprising tissue and/or cells;

B) obtaining a sample image of each of the at least one patient sample;

C) determining a total pixel number, chosen from a sum of abnormal pixel weights or a ratio of pixels, in the adjusted color range for each of the sample image;

D) classifying each of the at least one patient sample as belonging to the second category if the total pixel number in the sample image is below the at least one threshold, or classifying each of the patient samples as belonging to the first category if the total pixel number in the sample image is above or equal to the at least one threshold; and E) removing patient samples belonging to the second category from review, wherein step C) comprises an additional step of weighting pixels based on a distance to stain colored pixels in the first category, wherein a weight value is assigned to each pixel, which weight value is based on the distance from a closest of the stain colored pixels, wherein a low value is assigned if the pixel is close to the closest of the stain colored pixels, and a high value is assigned if the pixel is far from the closest of the stain colored pixels.

2. The method according to claim 1, wherein several patient samples contain cells from a same patient, and steps A)-D) are repeated for each patient sample, and wherein the method further comprises prior to step E):

aggregating results for patient samples containing cells from the same patient by re-classifying patient samples belonging to the second category as patient samples belonging to the first category if any of the patient samples is classified as belonging to the first category in step C).

3. The method according to claim 1, wherein the closest colored pixels comprises a red colored pixel.

4. The method according to claim 1, wherein step C) comprises the steps of:

C1) removing pixels in the sample image corresponding to a background area;

C2) counting remaining pixels in a sample area to obtain a total sample pixel count;

C3) removing pixels outside the adjusted color range from the sample image;

C4) counting remaining pixels in the color range to obtain a pixel count corresponding to colors in cells belonging to the first category;

C5) removing the pixels outside a red color range from the sample image; and

C6) calculating the total pixel number as a ratio of pixels in the color range for the sample image divided by a pixel count, corresponding to colors belonging to the first category by a total pixel count in the sample image.

5. The method according to claim 4, further comprising the steps of:

locating pixels in a pre-determined exclusion color range;

reducing influence of said located pixels in step C4) when counting the remaining pixels in the sample image to obtain the pixel count corresponding to colors in cells belonging to the first category.

6. The method according to claim 1, wherein remaining pixels correspond to pixels within the color range, wherein step C) comprises the steps of:

C11) removing pixels in the sample image corresponding to a background area;

C12) removing the pixels outside a retrieved color range from the sample image

C13) optionally removing the pixels outside a red color range from the sample image;

C14) assigning remaining pixels into groups, such that all remaining pixels belonging to the group are within a maximum distance from other remaining pixels in that group, and each group is within a minimum distance away from all remaining pixels not belonging to that group;

C15) calculating the total pixel number for each group as a sum of abnormal pixel weights by summarizing all pixel weights of the remaining pixels of that group.

7. The method according to claim 6, wherein the at least one threshold is retrieved or is predetermined, wherein the at least one threshold is a first threshold and the first threshold is compared to each group of pixels in the sample image, and/or a second threshold is compared to a sum of all groups of pixels in the sample image, and/or a third threshold is compared to a size of a group of pixels in the sample image.

8. The method according to claim 1, wherein after step B and before step C, edges of the sample image are cut off in order to reduce a risk for samples being falsely classified as belonging to the first category.

9. A system for selection of tissue or cell samples comprising cells belonging to the first category in accordance with the method of claim 1, using at least one patient sample comprising tissue and/or cells being stained, the system comprising an image scanner configured to obtain the sample image of each patient sample, a second control unit and a data storage unit, wherein the second control unit is configured to:

retrieve the color range from the data storage unit;

determine a sum of abnormal pixel weights or a ratio of pixels in the color range for each of the sample images;

classify each patient sample as belonging to the second category if the sum of abnormal pixel weights or the ratio of pixels in the sample image is below a predetermined or retrieved at least one threshold, or classifying each patient sample as belonging to the first category if the sum of abnormal pixel weights or the ratio of pixels in the sample image is above or equal to the at least one threshold; and identify belonging to the second category patient samples to be removed from review.

10. A non-transitory storage medium storing a computer program for selection of tissue or cell samples comprising cells belonging to the first category, comprising instructions which, when executed on at least one processor, cause the at least one processor to carry out the method according to claim 1.

11. A computer-readable storage medium carrying a computer program for selection of tissue or cell samples according to claim 10.

* * * * *